US 6,677,366 B2
Jan. 13, 2004

(54) METHODS, COMPOSITIONS AND ARTICLES FOR REDUCING OR PREVENTING THE EFFECTS OF INFLAMMATION

(75) Inventors: Anna M. Richter, Vancouver (CA); Julia G. Levy, Vancouver (CA); Claude A. A. Hariton, Sillery (CA); Gustave Huber, Rafz (CH); William C. Stewart, James Island, SC (US); Mario G. Fsadni, Bulach (CH); Modestus O. K. Obochi, Vancouver (CA)

(73) Assignees: QLT Inc., Vancouver (CA); The University of British Columbia, Vancouver (CA); Novartis AG, Basel (CH)

( * ) Notice: Subject to any disclaimer, the term of this patent is extended or adjusted under 35 U.S.C. 154(b) by 109 days.

This patent is subject to a terminal disclaimer.

(21) Appl. No.: 09/929,558

(22) Filed: Aug. 13, 2001

(65) Prior Publication Data

US 2002/0103180 A1 Aug. 1, 2002

Related U.S. Application Data

(63) Continuation of application No. 08/942,883, filed on Oct. 2, 1997, now Pat. No. 6,274,614, which is a continuation of application No. 08/797,963, filed on Feb. 11, 1997, now abandoned.

(51) Int. Cl.$^7$ .............................................. A61K 31/40
(52) U.S. Cl. ...................................... 514/410; 514/912
(58) Field of Search .................................. 514/410, 912

(56) References Cited

U.S. PATENT DOCUMENTS

| | | |
|---|---|---|
| 4,932,934 A | 6/1990 | Dougherty et al. |
| 5,171,749 A | 12/1992 | Levy et al. ................ 514/410 |
| 5,283,255 A | 2/1994 | Levy et al. |
| 5,360,734 A | 11/1994 | Chapman et al. |
| 5,422,362 A | 6/1995 | Vincent et al. ............. 514/410 |
| 5,707,986 A | 1/1998 | Miller et al. ................ 514/185 |

FOREIGN PATENT DOCUMENTS

| | | |
|---|---|---|
| EP | 0 407 122 | 1/1991 |
| WO | WO 97/05127 | 2/1997 |
| WO | WO 97/33619 | 2/1997 |

OTHER PUBLICATIONS

Araujo et al., "A Ten–year Follow–up on a Prospective, Randomized Trial of Postoperative Corticosteroids after Traveculectomy", *Ophthalmology*, 102: 1753–59 (1995).
Berlin et al., The Role of Laser Sclerostomy in Glaucoma Surgery, *Current Opinion in Ophthalmology*, 6(II):102–114 (1995).
Chalfin et al., "Corneal Endothelial Toxic Effect Secondary to Fluorouracil Needle Bleb Revision", *Arch. Ophthalmol.*, 113:1093–94 (1993).
Fourman, "Scleritis after Glaucoma Filtering Surgery with mitomycin C", *Ophthalmology*, 102:10, 1569–71 (1995).
Freitas, "Inflammation and Photodynamic Therapy", *J. Photochem. and Photobiol., B:Biology*, 8: 340–41 (1991).
Gomer, C.J., et al., "Hematoporphyrin Derivative Photoradiation Therapy for the Treatment of Intraocular Tumors: Examination of Acute Normal Ocular Tissue Toxicity," *Cancer Research* (Feb. 1983) 43:721–727.
Hill et al., "Photodynamic Therapy (PDT) for Antifibrosis in a Rabbit Model of Filtration Surgery", *Investigative Ophthamology and Visual Science*, 36:4, S877 (1995).
Katz et al., "Mitomycin C versus 5–Fluorouracil in High–risk Glaucoma Filtering Surgery", *Ophthalmology*, 102:9, 1263–69 (1995).
Kay et al. "Delivery of Antifibroblast Agents as Adjuncts to Filtration Surgery–Part II:Delivery of 5–Fluorouracil and Bleomycin in a Collagen Implant: Pilot Study in the Rabbit", *Ophthalmolic Surg.*, 17:796–801 (1986).
Khaw et al., "Five–minute Treatments with Fluorouracil, Floxuridine, and Mitomycin Have Long–term Effects on Human Tenon's Capsule Fibroblasts", *Arch. Ophthalmol.*, 110:1150–54 (1992).

(List continued on next page.)

*Primary Examiner*—Zohreh Fay
(74) *Attorney, Agent, or Firm*—Morrison & Foerster LLP

(57) ABSTRACT

A method for reducing or preventing the effects of inflammation arising from injured tissue, which method comprises the steps of:

a. bringing the injured tissue, or pre-injured tissue, into contact with a photosensitizing agent capable of penetrating into the tissue, resulting in the desired degree of biodistribution in less than one hour; and b. exposing the tissue thus contacted to light having a wavelength absorbed by the photosensitizing agent for a time sufficient to reduce or prevent inflammation in the exposed tissue, but not so long as to cause necrosis or erythema of the exposed tissue, or a pharmaceutical composition or an article for reducing or preventing the effects of inflammation arising from injured tissue.

The composition comprises:

a. from about 1 μg/mL to about 2 mg/mL of a photosensitizing agent capable of penetrating into the injured tissue, or pre-injured tissue, resulting in the desired degree of biodistribution less than one hour; and b. a pharmaceutically acceptable carrier.

The article comprises:

a. a photosensitizing agent capable of penetrating into the injured tissue, or pre-injured tissue, resulting in the desired degree of biodistribution in less than one hour; and b. an absorbent applicator.

17 Claims, 8 Drawing Sheets

OTHER PUBLICATIONS

Khaw et al, "Effects of Inoperative 5–Fluorouracil or Mitomycin C on Glaucoma Filtration Surgery in the Rabbit", *Ophthalmology, 100*:367–72 (1993).

Klein, "Defense Reactions in Action", *Immunology, The Science of Self–Nonself Discrimination*, Chapter 14, 577–84 (1982).

Kupin et al., "Adjunctive Mitomycin C in Primary Trabeculectomy in Phakic Eyes", *Am. J. of Ophthalmology, 119*:30–39 (1995).

Lee et al., "Effects of Cytosine Arabinoside–impregnated Bioerodible Polymers on Glaucoma Filtration Surgery in Rabbits", *J. Glaucoma, 2*:96–100 (1993).

Levy, Semin. Oncol. (1994) 21(6, Suppl. 15):4–10.

Liang et al. "Comparison of Mitomycin C and 5–Fluorouracil on Filtration Surgery Success in Rabbit Eyes", *J. Glaucoma, 1*:87–93 (1992).

Margaron, P., et al., "Photodynamic therapy inhibits cell adhesion without altering integrin expression," *Biochimica et Biophysica Acta* (1997) 1359:200–210.

Mora et al., "Trabeculectomy with Intraoperative Sponge 5–Fluorouracil", *Ophthalmology, 103*:963–70 (1996).

Nouri–Mahdavi et al., "Outcomes of Trabeculectomy for Primary Open–angle Glaucoma", *Ophthalmology, 102*:12, 1760–69 (1995).

Shin et al., "Adjunctive Subconjunctival Mitomycin C in Glaucoma Triple Procedure", *Ophthalmology, 102*:10, 1550–58 (1995).

Simkin, G.O., et al., "Inhibition of contact hypersensitivity with different analogs of benzoporphyrin derivative," *Immunopharmacology* (1997) 37:221–230.

Stewart, "Filtering Surgery—Techniques and Operative Complications", *Clinical Practice of Glaucoma*, Chapter 10, 333–61 (1990).

Stewart, "Postoperative Complications of Filtering Surgery", *Clinical Practice of Glaucoma*, Chapter 11, 363–90 (1990).

Straight, R.C., et al., "Preliminary studies with implanted polyvinyl alcohol sponges as a model for studying the role of neointerstitial and neovascular compartments of tumors in the localization, retention and photodynamic effects of photosensitizers," *Advances in Experimental Medicine and Biology* (1985) 193:77–89.

Zacharia et al., "Ocular Hypotony after Trabeculectomy with Mitomycin C", *Am. J. of Ophthalmology, 116*:314–26 (1993).

Zhou, "Mechanisms of Tumor Necrosis Induced by Photodynamic Therapy", *J. of Photochem. and Photobiol., B: Biology, 3*, 299–318 (1989).

FORMULA 1

FORMULA 2

FORMULA 3

FORMULA 4

FORMULA 5

FORMULA 6

METHODS, COMPOSITIONS AND ARTICLES FOR REDUCING OR PREVENTING THE EFFECTS OF INFLAMMATION

This application is a continuation of U.S. patent application Ser. No. 08/942,883, filed Oct. 2, 1997, now U.S. Pat. No. 6,274,614, which is a continuation of U.S. patent application Ser. No. 08/797,963, filed Feb. 11, 1997, now abandoned.

TECHNICAL FIELD

This invention relates generally to the field of pharmacotherapeutics and the use of photodynamic therapy ("PDT") to reduce or prevent inflammation due to injured tissue, whether by intestinal injury, such as surgery, or by accidental injury, such as skin lacerations, injuries to joints and tendons, and the treatment of burn victims. In a preferred embodiment, the invention relates to the use of "low dose" PDT to treat ocular tissue where inflammation is due to the manipulation of eye tissue, especially when the inflammation presents a complicating factor in the patient's recovery from a necessary procedure. Common applications include inflammatory eye disease and various types of ocular surgery or laser treatment, such as transplantation and the filtration ocular surgery commonly used to treat glaucoma. In a particularly preferred embodiment, the invention relates to the extension of filtration bleb survival to improve the outcome of filtration surgery.

BACKGROUND ART

Inflammation in General

The four cardinal signs commonly associated with inflammation are: (1) redness, (2) swelling, (3) heat and (4) pain, with an optional fifth cardinal sign being loss of function of the affected part. While injury triggers a complex series of events, many of which occur simultaneously and are interrelated in a variety of ways, it is known that small blood vessels participate in an important way in the induction of inflammation. In fact, inflammation is one of the body's valuable defense mechanisms and is generally thought of as having three phases: the degenerative phase, the vascular phase, and the healing phase. See Klein, "Defense Reactions in Action", *Immunology, The Science of Self-Nonself Discrimination*, Chapter 14, 577–84 (1982), the disclosure of which is hereby incorporated by reference.

Specifically, in the degenerative phase, the affected cells, primarily epidermal cells and fibroblasts become swollen, with their cytoplasms becoming vacuolized and their nuclei enlarging and fragmenting. Some of the platelets in the damaged blood vessels disintegrate and release serotonin and other mediators acting on sympathetic nerve endings.

The vascular phase is characterized by changes in the blood vessels, extensive migration and activity of the so-called inflammatory cells (granulocytes—particularly neutrophils, lymphocytes, monocytes and macrophages), and the clearing of degenerated cells and cellular debris. The capillary network and the postcapillary venules become flooded, congested and engorged by blood in active hyperemia. Because the number of capillaries also proliferate, one observes the reddish appearance of inflamed tissue, sometimes called "flare." The increased blood flow also causes the temperature of the inflamed area to approach that of warmer aortic blood, as compared with the surrounding normal tissue, giving the sensation of heat.

Upon injury, the damaged tissue releases substances known to be related to histamine called H substances, which are a mixture of histamine and serotonin released by disrupted tissue mast cells. The H substances cause an active dilation of blood vessels, and the endothelial cells of the dilated vessel separate from one another, causing the gaps between them to enlarge. The endothelium lining the blood vessels gradually becomes paved with leukocytes, forcing some of the fluid out into the surrounding tissue. The protein-rich fluid that leaks out of the vessel into the surrounding tissue causes tissue swelling. The leakage of fluid also contains substances that neutralize bacterial toxins and aid in the destruction of the agent causing the inflammation.

The leukocytes, particularly neutrophils and monocytes, move about on the blood vessel wall until they find a suitable gap through which they can emigrate into the perivascular structures and tissue spaces. The leukocytes attack the dead and dying cells, digesting them intracellularly by phagocytosis or extracellularly by proteolytic enzymes released from their lysosomes when they themselves die. The stimuli for leukocyte emigration is believed to come from the injured tissue in the form of chemotactic factors.

Platelets are another cell type profoundly affected by tissue injury. Shortly after the injury, platelets, singly or in clumps, adhere to the vessel walls. Simultaneously, fibrin fibers begin to appear, forming a fine mesh that helps to trap cells. The resulting clot pulls the edges of the disrupted tissue together.

The intra- and extracellular digestion of necrotic tissue by neutrophils and monocytes produces a fluid that combines with the serous material being extruded from the blood vessels. If an abscess forms, the cavity is lined by a pyrogenic membrane that, in wounds infected with bacteria, prevents the dissemination and multiplication of pathogenic microorganisms into the blood.

In the first two phases of the inflammatory process, the foreign body is either destroyed, for example, if the foreign body is an organism, or the tissue around it is loosened, for example, if it is a splinter. In the healing phase, the inflammation begins to subside; individual blood vessels and vascular patterns become normal once again; and repair of the wound commences. The three main events in the repair process are (1) formation of new connective tissue by proliferating fibroblasts; (2) regeneration of epithelium; and (3) outgrowth of new capillaries.

Even before the inflammation subsides, fibroblasts begin moving into the injured area from the surrounding normal tissue, where they usually exist in a dormant state. They migrate by an ameboid movement along strands of fibrin and distribute themselves throughout the healing area. Once fixed into position in the injured tissue, they begin to synthesize collagen and secrete this protein, which arranges itself into fibers. The fibers orient themselves with their longitudinal axes in the direction of the greatest stress. As the collagen bundles grow in firmness, the fibroblasts gradually degenerate and attach closely to the bundles, and the injured area transforms into scar tissue.

Simultaneously with scar tissue formation, the intact epidermal cells on the edge of the wound begin to proliferate and move, as one sheet, toward the center of the injured area. As the inflammation subsides, a need for a direct supply of blood arises, and new vessels begin to grow into the wound.

It is known that, looking at inflammation on a molecular basis, a number of active compounds interact with one another in a complex manner. Among the cells damaged by injury are mast cells, which release mediators that trigger an early phase of vasodilation, accompanied by the separation of endothelial cells and exposure of collagen fibers in the subendothelial layer. Fibers in the intercellular gaps that form in blood vessels trap platelets and trigger the release of mediators from these cells.

In addition to platelets, the exposed collagen fibers also interact with proteins of the plasma that filter through the pores of the dilated vessel wall, including the triggering factor of the blood-clotting cascade. These proteins also initiate the kinin-bradykinin cascade, producing bradykinin, which becomes involved in vasodilation, the increase of blood vessel permeability, and chemotaxis.

A fourth molecular system, the complement cascade, can be activated by several stimuli: the injured blood vessels, the proteolytic enzymes released by the damaged cells, the membrane components of any participating bacteria, and antigen-antibody complexes. Some of the activated complement components act as chemotactic factors, responsible for the influx of leukocytes into the inflamed area. Others facilitate phagocytosis and participate in cell lysis.

Ocular Inflammation

Glaucoma is a disease of the eye in which high intraocular pressure causes damage to the individual's vision. In a normal eye, fluid is produced by the epithelial cells of the ciliary body, which is located around the inner circumference of the iris (toward the inside of the eyeball). The functions of this fluid include nourishing the cells in the eye and keeping a positive pressure within the eyeball, which is necessary for maintaining the correct spatial distribution of the visual parts needed for image formation, similar to the supporting structure of a camera body in a photographic camera.

The fluid is normally removed from the eye by filtration through the trabecular meshwork, a circular body placed circumferentially in the angle between the iris and the cornea in the anterior portion of the eye. The fluid typically drains through microscopic holes in the trabecular meshwork into Schlemm's canal, and then through connector channels that lead the fluid into the episcleral veins and out of the eye. In the pathology of glaucoma, the outflow of the fluid from the eye is reduced, resulting in a sharp increase in intraocular pressure, damage to the inner eye tissues and, eventually, the complete loss of vision.

The therapeutic objective in treating glaucoma is always the same, i.e., to lower the intraocular pressure, either by decreasing fluid production or by increasing the drainage or "filtration" of the fluid out of the eye. While there are many means to accomplish this objective, medication is always tried first. If medication is not successful in controlling the elevated intraocular pressure, other more invasive techniques are used, such as laser treatment or surgical intervention.

Laser procedures include trabeculoplasty, in which the laser is used to burn holes in the trabecular meshwork. Surgical techniques include (1) a trabeculotomy, which uses a metal probe or "trabeculotom" to create an opening between Schlemm's canal and the anterior chamber of the eye for roughly one third of the circumference of the normal drainage angle; (2) a trabeculectomy, which involves cutting through the trabecular meshwork; and (3) an iridectomy which refers to the cutting out of portions of the iris. A sclerostomy involves cutting through the sclera with either a laser or a surgical instrument. Trabeculectomy, iridectomy and sclerostomy are all associated with the formation of a filtration "bleb", a small bladder into which excess ocular fluid is shunted to expedite drainage away from the eye.

Glaucoma filtering surgery is usually recommended for patients who have progressive glaucomatous damage and those who, at their current level of ocular pressure, are at a significant risk for progression of the disease. For patients with severe damage, the long-term prognosis is improved when the intraocular pressure ("IOP") can be reduced to less than 20 mm Hg and maintained below this level. Thus, in patients with advanced damage and ocular pressures above 18–20 mm Hg, filtering surgery is usually strongly recommended.

The surgery generally falls into one of two categories: (1) full thickness procedures or (2) guarded fistula procedures. The more basic, guarded fistula procedure typically involves the following trabeculectomy steps:

a. retracting the eyelid;
b. penetrating the limbus (a translucent tissue that represents the transition between the opaque sclera and the clear cornea of the eye) to produce an opening into the anterior chamber (bounded by the colored iris and the clear cornea covering the iris) from the outside of the anterior portion of the eye;
c. at a point below the iris, peeling back the outer layers of the conjunctiva and cutting a triangular scleral flap with the base of the triangle at the limbus;
d. entering the anterior chamber from the base of the triangular scleral flap;
e. excising a portion of the underlying trabecular meshwork to form a fistula, or connecting channel;
f. excising a small portion of the iris through the fistula;
g. using sutures to close the scleral flap;
h. suturing closed the conjunctiva; and
i. injecting a physiologically acceptable fluid, such as basic salt solution ("BSS"), into the anterior chamber through the exterior opening penetrating the limbus, which was made in step b, to elevate the bleb formed along the limbus, to confirm that the fistula is not blocked, and to confirm that there are no leaks in the bleb.

The full thickness procedure differs in that a direct opening, without the scleral flap, is created to connect the anterior chamber to the subconjunctival space through the limbus. After the outer layers of the conjunctiva have been peeled back, the fistula is created by sclerectomy (cutting a lip of tissue out of sclera at the limbus), thermal sclerostomy (cutting a shallow groove in the sclera parallel to the limbal surface), laser sclerostomy, or trephination. Stewart, "Filtering Surgery—Techniques and Operative Complications", *Clinical Practice of Glaucoma*, Chapter 10, 333–61 (1990), the disclosure of which is hereby incorporated by reference.

Following surgery, the condition of the filtration bleb is carefully observed on a regular basis. Initially, the bleb is usually well-elevated off from the sclera. Many eyes show a beginning area of avascularity in the conjunctiva the first day postoperative, usually around the fistula site. The avascular area is identified by noting a localized loss of capillaries and venules. However, when examining the anterior chamber, a small amount of redness or flare may be present, indicating inflammation. The IOP in the first postoperative week is usually less than 5 mm Hg, although it may be in the 6–10 mm Hg range. After the initial examination, the patient is typically started on an antibiotic-steroid combination. Stewart, "Postoperative Complications of Filtering Surgery", *Clinical Practice of Glaucoma*, Chapter 11, 363–90 (1990), the disclosure of which is incorporated herein by reference.

In the second to fourth postoperative week, the conjunctiva and the bleb become less inflamed, and the anterior chamber becomes "quiet" as the amount of flare subsides. Also, as a result of scarring, the bleb usually becomes a little smaller. Additionally, the bleb generally continues to show an avascular area that may increase in size. The IOP in the second to fourth postoperative week usually rises to 10 mm Hg or above. Stewart, "Postoperative Complications of Filtering Surgery", *Clinical Practice of Glaucoma*, Chapter 11, 363–90 (1990).

After four weeks of an uncomplicated post-operative course, the conjunctiva usually has little or no inflammation. The well-functioning bleb typically maintains an avascular area and may either be minimally or well-elevated off the sclera. Additionally, the IOP should stabilize during this period, ideally between 10 and 15 mm Hg. Topical postoperative steroids are tapered slowly, according to the amount of inflammation in the filtering bleb and the anterior chamber. If the bleb remains vascular and inflamed, steroids are commonly maintained, and sometimes even increased, to hasten the resolution of any anterior segment inflammation, thus limiting scar formation. Stewart, "Postoperative Complications of Filtering Surgery", *Clinical Practice of Glaucoma*, Chapter 11, 363–90 (1990).

Unfortunately, during the early postoperative period after filtration surgery, a patient may suffer a variety of different complications, one of which is bleb failure. In many patients, bleb failure occurs between 1–6 months postoperatively, and the bleb ultimately fails to control the ocular pressure Clinically, filtering blebs that are functioning poorly are usually small in extent, are poorly elevated, and become at least partially vascularized, and the IOP again becomes elevated above the normal range. Stewart, "Postoperative Complications of Filtering Surgery", *Clinical Practice of Glaucoma*, Chapter 11, 363–90 (1990).

The success of filtering surgery depends upon how long after the surgery the bleb remains functional. Patients typically develop bleb failure from either a blockage at the fistula site or from scarring at the interface between the conjunctiva and the sclera. If the fistula site is blocked, one of several laser therapy techniques or conventional surgical techniques may be used. Unfortunately, however, even if the fistula is thus opened, the aqueous outflow may be limited due to previous bleb scarring to the sclera. If these procedures fail and the patient's IOP is uncontrolled on maximal medical therapy, performing another filtering procedure at a different location may be necessary. If the fistula remains open but the bleb is small, the increased IOP probably has resulted from scarring between the conjunctiva and the sclera, which remains the most common cause of bleb failure. Stewart, "Postoperative Complications of Filtering Surgery", *Clinical Practice of Glaucoma*, Chapter 11, 363–90 (1990).

The manipulation of the eye tissues, especially conjunctiva, in filtering surgery necessarily causes inflammation and, eventually, scarring. In general, the more the manipulation, the shorter the bleb survival time. Because filtering surgery in patients at high risk for glaucoma often results in failure as a result of postoperative scarring, fibroblasts appear to play a critical role in this process. Katz et al, "Mitomycin C versus 5-Fluorouracil in High-risk Glaucoma Filtering Surgery", *Ophthalmology*, 102:9, 1263–68 (1995). One of the primary reasons for failure in glaucoma filtration surgery is the presence of fibroblasts in subconjunctival tissue, (Berlin et al, "The Role of Laser Sclerostomy in Glaucoma Surgery", *Current Opinion in Ophthalmology*, 6:102–114 (1995)), and when the operation fails, it is usually because there has been fibroblast proliferation and scarring at the filtration site (Mora et al., "Trabeculectomy with Intraoperative Sponge 5-Fluorouracil", *Ophthalmology*, 103:963–70 (1996)).

In so-called "high risk" patients, where there is a high percentage of bleb failures due to fibrosis, sometimes treatment concomitant with the surgery to extend the survival of the filtering bleb is helpful. Many techniques have been devised to reduce inflammation and scarring, thus prolonging the function of the filtering bleb created in filtering surgery, such as simple digital massage of the eye on a periodic basis for about four weeks following surgery.

Pharmacologic techniques to limit scarring by inhibiting the inflammatory response and preventing the formation of collagen at specific steps along its synthetic pathway have also been tried. Corticosteroids are often used, either topically as drops or injected subconjunctivally, to help prevent scarring of the bleb by inhibiting the inflammatory response and fibroblast proliferation. Stewart, "Filtering Surgery—Techniques and Operative Complications", *Clinical Practice of Glaucoma*, Chapter 10, 333–61 (1990). Usually, topical steroids are continued to minimize scarring until the anterior segment inflammation resolves. Stewart, "Postoperative Complications of Filtering Surgery", *Clinical Practice of Glaucoma*, Chapter 11, 363–90 (1990). A typical treatment program might indicate post-operative use topically every three hours with rapid tapering over 20 or so days. Araujo et al., "A Ten-year Follow-up on a Prospective, Randomized Trial of Postoperative Corticosteroids after Traveculectomy", *Ophthalmology*, 102:1753–59 (1995).

5-Fluorouracil ("5-FU") is a fluorinated pyrimidine analog with antimetabolic activity (a competitive inhibitor of thymidylate synthase), which also exerts an anti-fibrotic effect by decreasing fibroblast proliferation, thus preventing the scarring of the filtering bleb. Typically, 5-FU has been used in cases with poor surgical prognoses. At the two-year point, 5-FU has shown a success rate for filtering surgery between 60 and 70%. 5-FU is usually administered by a series of subconjunctival injections.

However, in addition to the inconvenience and discomfort of frequent and repeated postoperative injections, a number of serious complications have been reported with subconjunctival 5-FU, including epithelial defects, subepithelial scarring, corneal ulcerations, conjunctival wound leaks, bleb leaks, suprachoroidal hemorrhage, retinal detachment and endophthalmitis. Thus, although 5-FU can prolong bleb life, the incidence of corneal epithelial defects, scarring, and vascularization is also high due to the general toxicity of this agent. Stewart, "Filtering Surgery—Techniques and Operative Complications", *Clinical Practice of Glaucoma*, Chapter 10, 333–61 (1990). See also Khaw et al., "Five-minute Treatments with Fluorouracil, Floxuridine, and Mitomycin Have Long-term Effects on Human Tenon's Capsule Fibroblasts", *Arch. Ophthalmol.*, 110:1150–54 (1992); Kupin et al., "Adjunctive Mitomycin C in Primary Trabeculectomy in Phakic Eyes", *Am. J. of Ophthalmology*, 119:30–39 (1995); and Katz et al., "Mitomycin C versus 5-Fluorouracil in High-risk Glaucoma Filtering Surgery", *Ophthalmology*, 102:9, 1263–69 (1995). See also Kay et al. "Delivery of Antifibroblast Agents as Adjuncts to Filtration Surgery-Part II: Delivery of 5-Fluorouracil and Bleomycin in a Collagen Implant: Pilot Study in the Rabbit", *Ophthalmic Surg.*, 17:796–801(1986); and Khaw et al, "Effects of Inoperative 5-Fluorouracil or Mitomycin C on Glaucoma Filtration Surgery in the Rabbit", *Ophthalmology*, 100:367–72 (1993).

Some writers have reported that corneal edema due to inadvertent intraocular exposure could be prevented by the use of a lower concentration, e.g., 0.5 mL of 10 mg/mL 5-FU, in the usual subconjunctival injections. Chalfin et al., "Corneal Endothelial Toxic Effect Secondary to Fluorouracil Needle Bleb Revision", *Arch. Ophthalmol.*, 113:1093–94 (1993). Others have noted that the use of 5-FU can be made safer and more effective by intraoperative administration using a sponge soaked with 50 mg/mL of the compound and leaving the sponge in contact with the bleb site for a short period of time. Mora et al., "Trabeculectomy with Intraoperative Sponge 5-Fluorouracil", *Ophthalmology*, 103:963–970 (1996). However, even then, supplemental postoperative injections are needed in some cases, and their injections are still associated with an undesirably high incidence of corneal epithelial damage.

The deoxyribose sugar of fluorouracil, floxuridine, is about 100 times as potent as fluorouracil in long-term inhibition of ocular fibroblasts, and so can be given as a single dose. However, the difference between causing cell death, rather than inhibition, is relatively small. Therefore, the use of floxuridine is susceptible to the danger of exposing normal tissues to relatively high doses of potentially cytotoxic materials. Khaw et al., "Five-minute Treatments with Fluorouracil, Floxuridine, and Mitomycin Have Long-term Effects on Human Tenon's Capsule Fibroblasts", *Arch. Ophthalmol.*, 110:1150–54 (1992).

Similar effects have been noted with mitomycin or mitomycin C ("MMC"). Because it is much more potent than 5-FU, MMC can also be administered in a single intraoperative application, typically with a contact time of about one to five minutes, followed by copious irrigation. MMC is an alkylating antiproliferative agent isolated from the fermentation filtrate of a particular species of Streptomyces. It is an anti-fibrotic, anti-neoplastic antibiotic that prevents the scarring of filtration blebs by inhibiting the proliferation of fibroblasts. It is usually effective in reducing postoperative subconjunctival fibrosis and, thus, tends to lengthen the survival time of filtration blebs and to reduce the IOP.

However, MMC is also cytocidal at high concentrations and produces undesirable ocular hypotony (IOP less than 5 or 6 mm Hg) in as much as ⅓ of the patients treated with it. Other undesirable side effects include conjunctival wound leaks, choroidal detachments, and hypotony maculopathy, with a probability of late-onset bleb leaks of around 25% See Khaw et al., "Five-minute Treatments with Fluorouracil, Floxuridine, and Mitomycin Have Long-term Effects on Human Tenon's Capsule Fibroblasts", *Arch. Ophthalmol.*, 110:1150–54 (1992); Zacharia et al., "Ocular Hypotony after Trabeculectomy with Mitomycin C", *Am. J. of Ophthalmology*, 116:314–26 (1993); Kupin et al., "Adjunctive Mitomycin C in Primary Trabeculectomy in Phakic Eyes", *Am. J. of Ophthalmology*, 119:30–39 (1995); Katz et al., "Mitomycin C versus 5-Fluorouracil in High-risk Glaucoma Filtering Surgery", *Ophthalmology*, 102:9, 1263–69 (1995); Shin et al., "Adjunctive Subconjunctival Mitomycin C in Glaucoma Triple Procedure", *Ophthalmology*, 102:10, 1550–58 (1995); Nouri-Mahdavi et al., "Outcomes of Trabeculectomy for Primary Open-angle Glaucoma", *Ophthalmology*, 102:12, 1760–69 (1995); and Mora et al., "Trabeculectomy with Intraoperative Sponge 5-Fluorouracil", *Ophthalmology*, 103:963–970 (1996). One group of investigators even reported an increased incidence of scleritis, involving severe pain and redness of the sclera, following topical treatment with MMC during trabeculectomy. Fourman, "Scleritis after Glaucoma Filtering Surgery with mitomycin C", *Ophthalmology*, 102:10, 1569–71 (1995). See also Liang et al. "Comparison of Mitomycin C and 5-Fluorouracil on Filtration Surgery Success in Rabbit Eyes", *J. Glaucoma*, 1:87–93 (1992).

Other scientists have reported the use of laser sclerostomy along with either 5-FU or MMC. While the use of 5-FU administered after laser treatment over a two-week period was described as successful by Berlin et al., "The Role of Laser Sclerostomy in Glaucoma Surgery", *Current Opinion in Ophthalmology*, 6:11, 102–114 (1995), it was suggested that the use of MMC administered by a number of different channels (subconjunctival injection, subconjunctival gel foam, topical drops or by absorbent sponges), along with laser treatment, could be even more effective. However, the usual complications were also noted, i.e., corneal toxicity, wound leak, chronic hypotony, choroidal detachment, and hyotonous maculopathy.

Beta-aminopropionitrile ("BAPN") and D-penicillamine have been used to inhibit the cross-linking of collagen fibers, which may help to keep collagen in an immature state after filtration surgery and, consequently, limit bleb scarring. An initial report using topical BAPN ointment postoperatively found that it kept the IOP below 22 mm Hg in 74% of the patients. However, animal studies using both BAPN and D-penicillamine showed only limited potency. Stewart, "Filtering Surgery—Techniques and Operative Complications", *Clinical Practice of Glaucoma*, Chapter 10, 333–61 (1990).

For a discussion of bleomycin, see Khaw et al., "Effects of Inoperative 5-Fluorouracil or Mitomycin C on Glaucoma Filtration Surgery in the Rabbit", *Ophthalmology*, 100:367–72 (1993). For a discussion of cytosine arabinocide-impregnated polymers, see Lee et al., "Effects of Cytosine Arabinoside-impregnated Bioerodible Polymers on Glaucoma Filtration Surgery in Rabbits", *J. Glaucoma*, 2:96–100 (1993).

Photodynamic Therapy

Photodynamic therapy ("PDT") is known as an approved cancer treatment that can be used for many purposes, such as the treatment of solid tumors (e.g., U.S. Pat. Nos. 4,932,934 and 5,283,255); the impairment of blood-borne targets such as leukemic cells, immunoreactive cells (copending application Ser. Nos. 07/889,707; 08/309,509, 08/374,158 and 08/174,211), and unwanted microorganisms (U.S. Pat. No. 5,360,734); the prevention of restenosis (U.S. Pat. No. 5,422,362); the diagnosis and treatment of certain neovascular ocular disorders (co-pending application Ser. Nos. 08/209,473, 08/390,591 and 08/613,420); the removal of atherosclerotic plaque (co-pending application Ser. No. 08/663,890); and the prevention of transplant rejection (co-pending application Ser. No. 08/371,707).

PDT involves the local or systemic application of a light-absorbing photosensitive agent, usually a porphyrin derivative, which accumulates selectively in target tissues. Upon irradiation with visible light of an activating wavelength, reactive oxygen species are produced in cells containing the photosensitizer, which promote cell death. For example, in the treatment of tumors, the photosensitization process is thought to give rise to singlet oxygen, an activated derivative of molecular oxygen, which may oxidatively react with a number of specific sites in cells and tissues. As a consequence, the tumor cells undergo irreversible damage at a subcellular levels, especially in the cell membrane and mitochondria. In vivo, tumor destruction is the result of a complex interplay of multiple factors affecting the framework of connective tissue that physically supports the stroma of a tumor and the vascular tissue that nourishes the tumor. Zhou, "Mechanisms of Tumor Necrosis Induced by Photodynamic Therapy", *J. of Photochem. and Photobiol., B: Biology*, 3, 299–318 (1989).

It is clear that photosensitizers are preferentially taken up and accumulate in tumor tissue and that some tumor stroma cell necrosis is selectively and directly caused by PDT. However, vascular injury and the subsequent anoxia of tumor cells are also involved in the tumor necrotizing process induced by PDT. Particularly in this latter event, PDT-induced tumor necrosis has been considered the result of an acute inflammatory reaction to the physicochemical changes in the vascular wall. The rapid reduction in blood supply, as well as the onset of inflammatory edema in the tumor, leads to hypoxia or even anoxia of the photoinjured neoplastic cells, which eventually undergo necrosis. The overall damaging process is multiplied by the release of vasoactive or tissue-lysing substances such as histamine, proteases and acid phosphatases from photodamaged mast cells and neutrophils in the tumor stroma, which are also associated with inflammatory processes. Zhou, "Mechanisms of Tumor Necrosis Induced by Photodynamic Therapy", *J. of Photochem. and Photobiol., B: Biology*, 3, 299–318 (1989).

It has been recognized that the acute inflammatory phase usually induced by PDT in approved cancer treating protocols is a double-edged sword. The study of experimental tumor models has shown that, after PDT is administered, a protein- and neutral lipid-rich exudate infiltrates into the extracellular space and accumulates against a "wall" of perinecrotic vital cells ("hypoxic cells"), which are stuck against the "ghosts" of necrotic cells. From a positive cancer treatment perspective, the inflammatory exudate may help to deliver protein-bound photosensitizers to the inner areas of the tumor that would otherwise be difficult to reach. On the other hand, this flow of inflammatory exudate may also bring oxygen and nutrients and thus help to nourish cells engaged in wound repair processes. Therefore, the occurrence of an inflammatory state associated with PDT has been recognized a fact of life that often complicates the treatment of cancerous tumors. Freitas, "Inflammation and Photodynamic Therapy", *J. Photochem. and Photobiol., B: Biology*, 8: 340–41 (1991).

Some work has been done with PDT to achieve an antifibrosis effect in connection with glaucoma filtering surgery using tin ethyl etiopurpurin ("SnET2") as the photosensitive agent. Specifically, rabbits that received subconjunctival injections of SnET2 underwent filtering surgery followed by post-operative light irradiation. Hill et al., "Photodynamic Therapy with Tin Ethyl Etiopurpurin as an Alternative Anti-fribrotic Treatment Following Glaucoma Filtering Surgery", *Photochem. Photobiol*, 61 Suppl., 68S, TPM-E9 (1995); and Hill et al., "Photodynamic Therapy (PDT) for Antifibrosis in a Rabbit Model of Filtration Surgery", *Investigative Ophthalmology and Visual Science*, 36:4, S877 (1995). However, in this preliminary work, the authors do not report any control data and, therefore, it is difficult to determine how much the Hill et al. treatment actually prolonged the survival of the filtration bleb over untreated blebs.

Further, Hill et al. disclose that more than three hours elapsed after the injection of the photosensitive agent before the surgery and the irradiation step took place, which would have allowed sufficient time for the photosensitizer to be absorbed by the tissues associated with injury, but would also have allowed the photosensitizing agent to spread to other non-target areas of the eye. Because the authors report that large, transient areas of avascular conjunctiva were produced, with the avascular region not being limited to the filtration bleb until a full four weeks after the surgery, it is clear that undesirably large areas of the eye were affected by the treatment. In view of the well-known potentially destructive, necrotic effect of PDT in other applications, there is a need for the reduction or prevention of inflammation in such a way that the degree and extent of pharmacological activity can be reliably controlled.

DISCLOSURE OF THE INVENTION

Surprisingly, it has now been found that, with the appropriate choice of a photosensitizing agent that is rapidly absorbed by injured tissues, but non-toxic in the absence of light, PDT can have a predictable and beneficial anti-inflammatory effect that is useful even for delicate tissues, such as the eye area. This is a particularly surprising discovery in view of teachings in the past that PDT has been responsible for actually causing inflammatory responses, rather than having the ability to reduce or prevent them.

Specifically, it has now been discovered that the effects of inflammation arising from injured tissue can be reduced or prevented by low-dose PDT. Specifically, the method of the invention for reducing or preventing such inflammation comprises the steps of:

a. bringing the injured tissue, or pre-injured tissue, into contact with a photosensitizing agent capable of penetrating into the tissue, resulting in the desired degree of biodistribution in less than one hour; and b. exposing the tissue thus brought into contact to light having a wavelength absorbed by the photosensitizing agent for a time sufficient to reduce or prevent inflammation in the exposed tissue, but not so long as to cause necrosis or-erythema of the exposed tissue.

The method of the invention is particularly advantageous when the injured tissue is highly sensitive to further injury or inflammation, such as in ocular tissue, because appropriate photosensitizers are not, in themselves, antiproliferative in effect or cytotoxic to delicate tissues in the absence of activating irradiation. Further, because most photosensitizing agents are non-toxic to human tissue unless activated by light and because the photosensitizing agent of the invention is capable of penetrating into injured tissue relatively quickly, the degree of pharmacologic activity is easily controlled both by the extent of the irradiation and either the extent of physical contact with the photosensitizer or its concentration, e.g., in the bloodstream, at the time of irradiation. Consequently, the therapeutic effect of the invention is more easily regulated than known pharmacologic antifibrotic techniques.

In another embodiment, the invention relates to a composition for reducing or preventing the effects of inflammation arising from injured tissue comprising:

a. from about 1 $\mu$g/mL to about 2 mg/mL of a photosensitizing agent capable of penetrating into the injured tissue, or pre-injured tissue, resulting in the desired degree of biodistribution in less than about one hour and;

b. a pharmaceutically acceptable carrier.

In yet another embodiment, the invention relates to an article for reducing or preventing the effects of inflammation arising from injured tissue, which article comprises:

a. a photosensitizing agent capable of penetrating into the injured tissue, or pre-injured tissue, resulting in the desired degree of biodistribution in less than one hour; and b. an absorbent applicator.

DETAILED DESCRIPTION OF THE INVENTION

Figure 1A:
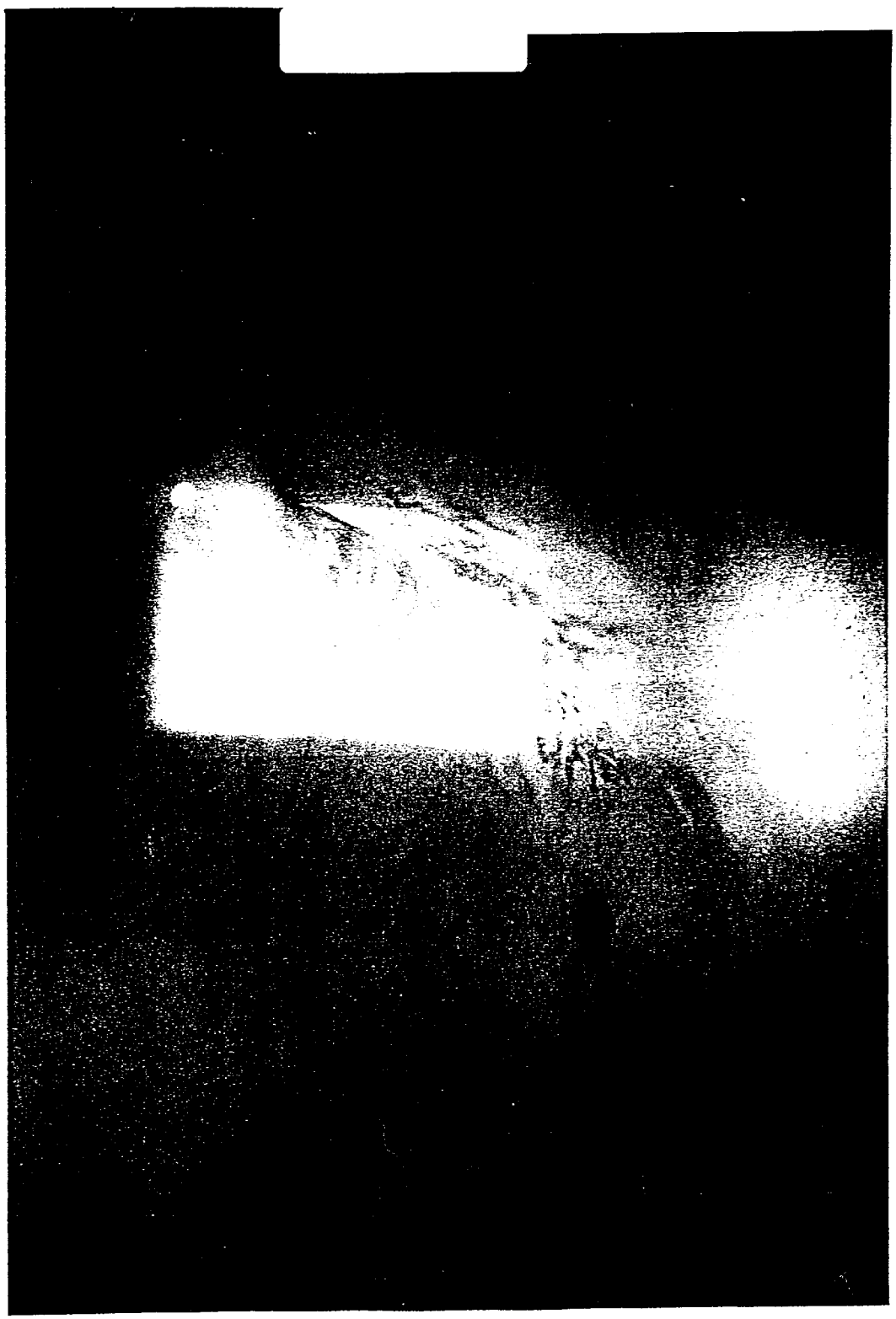
FIG. 1A shows a control, untreated bleb with prominent vascularity three days after surgery. (The experimental groups shown in FIGS. 1–5 are described in more detail in the working Examples of this application.)

The term "inflammation" in this application refers to the series of changes that occurs in a living body following an injury. The injury may be caused by physical agents, such as excessive heat or cold, pressure, ultraviolet or ionizing irradiation, cuts or abrasions; by a wide variety of inorganic or organic chemical substances; or by biological agents such as viruses, bacteria, and other parasites.

Photosensitizing Agent

A "photosensitizing agent" is a chemical compound that, when exposed to light of a wavelength capable of being absorbed by the photosensitizer, absorbs light energy to result in the desired physiological effect, e.g., a controlled anti-inflammatory effect. The photosensitizing agents of the present invention preferably have an absorption spectrum that is within the range of wavelengths between 350 nm and 1200 nm, which absorption spectrum may be tailored to the desired penetration in a manner known per se, preferably between about 400 and 900 nm and, most preferably, between 600 and 800 nm.

Another property of photosensitizers in general that is of particular significance in the practice of the present invention is a relative absence of toxicity to cells in the absence of the photochemical effect and the ready clearance from tissues in the absence of a target-specific interaction between particular cells and the photosensitizer.

The photosensitizer of the invention can be any photosensitizing agent suitable for photodynamic therapy ("PDT") that is capable of penetrating into the injured tissue to be treated and causing the desired degree of biodistribution in less than one hour. Whether this criterion is met by a potential photosensitizer candidate can be easily and quickly determined by the following simple test:

1. Prepare live cultured cells (preferably from a suspension grown culture; any cell line is suitable).
2. Add the photosensitizer being tested to the cells at concentrations of 1-3 ug/mL, in the presence of 10% serum.
3. Remove the excess photosensitizer drug by centrifugation following various periods of incubation (e.g., 5, 15, 30 and 60 minutes).
4. Wash the cells with phosphate-buffered saline and lyse them by freeze-thawing.
5. Determine the concentration of a tested photosensitizer in cell lysates by fluorescence against appropriate standards.

A particularly potent group of photosensitizers includes green porphyrins, which are described in detail in Levy et al., U.S. Pat. No. 5,171,749 issued Dec. 15, 1992, which is incorporated herein by reference. The term "green porphyrins" refers to porphyrin derivatives obtained by reacting a porphyrin nucleus with an alkyne in a Diels-Alder type reaction to obtain a mono-hydrobenzoporphyrin. Typically, green porphyrins are selected from a group of porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B).

Figure 6:
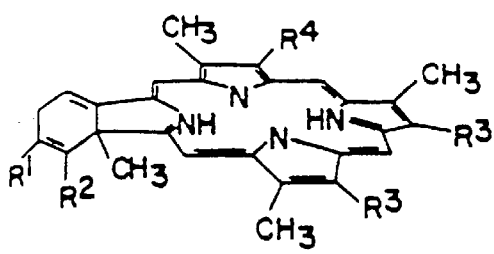
FIG. 6 shows the formulas of typical green porphyrins useful in the methods, compositions, and articles of the invention.
Figure 6:
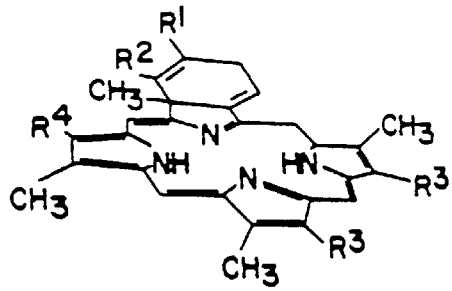
Figure 6:
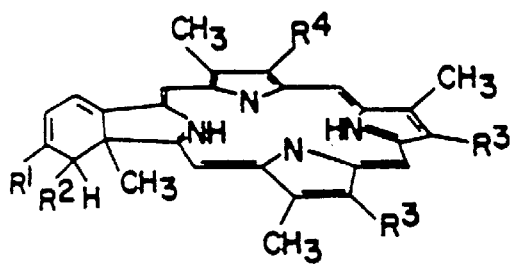
Figure 6:
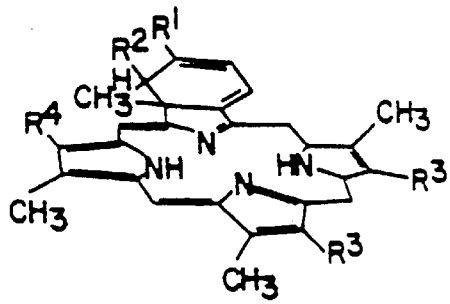
Figure 6:
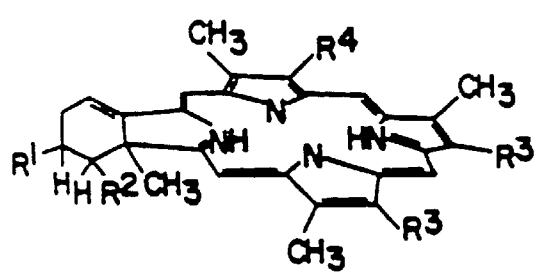
Figure 6:
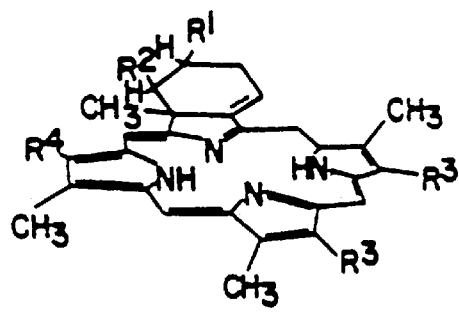
Figure 7A:
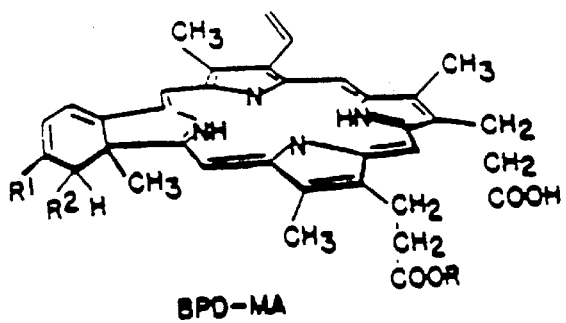
FIG. 7 shows the structure of four BPD-type compounds particularly useful as photosensitizing agents in the invention.
Figure 7B:
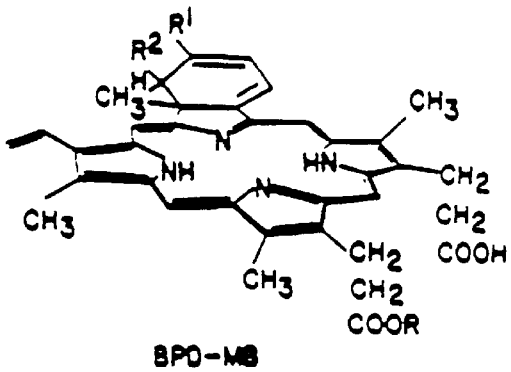
Figure 7C:
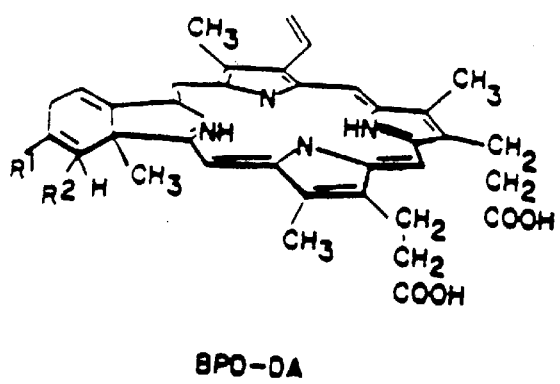
Figure 7D:
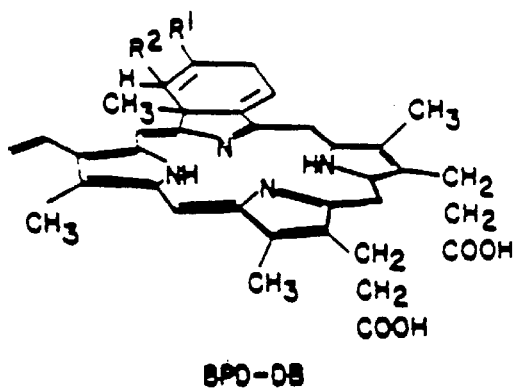

Several structures of typical green porphyrins are shown in FIG. 6. The Diels-Alder reaction initially results in the formation of a cyclohexadiene—referred to herein as "hydrobenzo"—fused to the A or B pyrrolic ring, as shown in formulas 1 and 2 of FIG. 6. Rearrangement of the π system in the hexadiene ring results in the formation of compounds of formulas 3 and 4, and reduction would provide compounds of formulas 5 and 6. For practical reasons, however, the compounds of formulas 5 and 6 are preferably made by performing the previously discussed Diels-Alder reaction with the corresponding olefin being substituted for the usual acetylene compound, thus producing a more reduced version of the resulting porphyrin ring structure. These compounds are shown in formulas 1–6 with hydrogen occupying the internal ring nitrogens. However, it is to be understood that the metalated forms, in which a cation replaces one or both of these hydrogens, can also be used. The preparation of the green porphyrin compounds useful in this invention is described in detail in U.S. Pat. No. 5,095,030.

For convenience, an abbreviation of the term hydromonobenzoporphyrin derivative—"BPD"—is generally used to refer to compounds of formulas 3 and 4 of FIG. 6. Compounds of the formulas 3 and 4 and mixtures thereof are particularly preferred.

As shown in FIG. 6, $R^1$, $R^2$, $R^3$ and $R^4$ are non-interfering substituents that do not appreciably affect the activity of the compound in the method and composition of the invention. More specifically, the term "non-interfering substituents" is used to mean substituents that do not destroy the ability of the green porphyrin to act as a photosensitizer capable of be absorbed by injured tissue to exert a pharmacological effect in less than one hour. For the compounds of FIGS. 6 and 7, generally, $R^1$ and $R^2$ are each, independently, electron-withdrawing substituents or any other activating substituents that are sufficiently electron-withdrawing to increase the rate of the Diels-Alder reaction, which can proceed with both A and B rings but, preferably, occurs in only one ring. Examples of suitable $R^1$ and $R^2$ groups include carbalkoxy (2–6C), alkyl (1–6C) sulfonyl or aryl (6–10C) sulfonyl, aryl (6–10C), cyano, and —CONR$^5$CO— where $R^5$ is aryl (6–10C) or alkyl (1–6). One of $R^1$ and $R^2$ may also be hydrogen, so long as the other is an electron-withdrawing substituent of sufficient strength to facilitate the Diels-Alder reaction. Most commonly, $R^1$ and $R^2$ are carbalkoxy groups, preferably methyl or ethyl carboxy esters. Preferred compounds are those in which $R^1$ and $R^2$ are the same and are carbalkoxy, particularly carboethoxy.

As used herein, the term "carboxy" is, as conventionally defined, —COOH, while "carbalkoxy" represents —COOR where R is alkyl. "Carboxyalkyl" refers to the substituent —R'—COOH where R' is alkylene. "Carbalkoxyalkyl" refers to —R'—COOR where R' is alkylene and R is alkyl or alkanol. "Alkyl" generally represents a saturated straight or branched chain hydrocarbyl moiety of 1–6 carbon atoms, such as methyl, n-hexyl, 2-methylpentyl, t-butyl, n-propyl, and so forth. "Alkylene" is the same as "alkyl" except that the group is divalent rather than monovalent. "Aryl" represents an aromatic cyclic group, such as phenyl, naphthyl, pyridyl, and the like. The aryl group of the invention is optionally substituted with 1–3 substituents, which may be independently selected from the group consisting of halo, such as fluoro, chloro, bromo or iodo; lower alkyl (1–4C); and lower alkoxy (1–4C). "Aryl" or "alkyl sulfonyl" groups have the formula —SO$_2$R where R is alkyl or aryl as defined above.

$R^3$ is independently a ω-carboxyalkyl group (2–6C) or a salt, amide, ester or acylhydrazone thereof, or is alkyl (1–6C). Preferably, $R^3$ is 2-carboxyethyl or the alkyl or alkanol ester thereof, and $R^4$ is vinyl. Most of these embodiments, however, are preferred because of the availability of native porphyrins, rather than being mandated by considerations of biological efficacy. As shown in FIG. 6, adducts formed by the reaction of $R^1$—C≡C—$R^2$ with a protoporphyrin-IX ring system (where $R^3$ is a protected form of 2-carboxyethyl, such as 2-carbomethoxyethyl or 2-carboethoxyethyl, and $R^4$ is —CH=CH$_2$) are compounds of the formulas 1 and 2. Compounds of formula 1 result from the addition to the A ring, and compounds of formula 2 result from the addition to the B ring.

Convenient starting materials for the green porphyrin compounds of the invention include the naturally-occurring porphyrins where $R^3$ is either —CH$_2$CH$_2$COOH, —CH$_2$CHRCONR$_2$ or —CH$_2$CHRCOOR where R is alkyl (1–6C) or alkanol (1–6C). However, the exact nature of $R^3$, unless it contains a π-bond conjugated to ring π-bond, is ordinarily not relevant to the progress of the Diels-Alder reaction or to the effectiveness of the resulting product. $R^3$ can thus be any one of a wide variety of groups such as, for example, lower alkyl (1–4C); and ω-carboxyalkyl (2–6C) and the esters and amides thereof The $R^3$ substituent may also be substituted with a hydroxy group; halogen, such as fluoro, chloro, bromo or iodo; or with other nonreactive substituents.

When $R^3$ is —CH$_2$CHR—COOR, it has been found advantageous to hydrolyze, or partially hydrolyze, the esterified carboxy group. Typically, the hydrolysis at the $R^3$-position conveniently occurs at a much faster rate than that of the ester groups of $R^1$ or $R^2$. Further, the solubility and biodistribution characteristics of the resulting compounds are more desirable than those of the unhydrolyzed form. Hydrolysis results in the diacid or monoacid products (or their salts).

In compounds of formulas 1 and 2, $R^4$ is usually —CH=CH$_2$, at least initially, but this vinyl group is readily derivatized to other embodiments of $R^4$ by the addition to, or oxidation of, the vinyl ring substituent of ring B or A in formula 1 or 2 respectively. Thus, $R^4$ can be any one of a wide variety of substituents that are consistent with that formed by a facile addition reaction. For example, an exemplary addition reagent may be of the form HX where H is added to the carbon adjacent to the ring to provide an $R^4$-position having the formula:

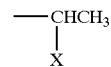

Thus, in one embodiment, one of the added substituents is a hydrogen, and the other one is selected from the group consisting of hydrogen; halo such as fluoro, chloro, bromo or iodo; hydroxy; lower alkoxy; amino; amide; sulfhydryl; or an organosulfide. For example, the Markovnikov addition of water provides a substituent structure analogous to a hematoporphyrin ring system at the relevant ring. The vinyl group can also be oxidized to obtain, as a substituent in the $R^4$-position, —CH$_2$OH, —CHO, or —COOH or its salts or esters. The addition or oxidation products can themselves also be substituted if the added substituents are functional leaving groups. For example, when Br is a substituent, it may be replaced by such moieties as —OH, —OR where R is alkyl (1–6C) as described above, halo, —NH$_2$, —NHR, —NR$_2$ and the like.

Thus, in general, $R^4$ represents any substituents to which the vinyl group —CH=CH$_2$ is readily converted by cleavage or addition, and further substituents formed by the reaction of leaving good groups with additional moieties. Preferably, however, $R^4$ is vinyl (—CH=CH$_2$); —CHOR$^{4'}$ where $R^{4'}$ is H or alkyl (1–6C), optionally substituted with a hydrophilic substituent such as —CH$_2$OH; —CHO; —COOR$^{4'}$ such as COOH or —COOCH$_3$; —CH(OR$^{4'}$)CH$_3$ such as —CH(OH)CH$_3$ or —CH(OCH$_3$)CH$_3$; —CH(OR$^{4'}$)CH$_2$OR$^{4'}$; —CH(OH)CH$_2$OH; —CH(SR$^{4'}$)CH$_3$ such as —CH(SCH$_3$)CH$_3$ and the disulfide thereof; —CH(NR$^{4'}$)CH$_3$; —CH(CN)CH$_3$; —CH(pyridinium bromide)CH$_3$; —CH(COOR$^{4'}$)CH$_3$; —CH(COOCR$^{4'}$)CH$_3$; —CH$_2$(halo)CH$_3$ such as —CHBrCH$_3$; or —CH(halo)CH$_2$(halo). Alternatively, $R^4$ can be an organic group of less than 12 carbon atoms resulting from the direct or indirect derivatization of vinyl. Or $R^4$ can provide additional porphyrin or porphyrin-related ring systems, such as a group containing from 1–3 tetrapyrrole-type nuclei of the formula —L—P, as defined below. Those compounds in which $R^4$ is —CH=CH$_2$, —CH(OH)CH$_3$, —CH(halo)CH$_3$, or a group containing 1–3 tetrapyrrole-type nuclei of the formula —L—P, as defined below, are preferred.

As used herein, the term "tetrapyrrole-type nucleus" represents a four-ring system of the skeleton:

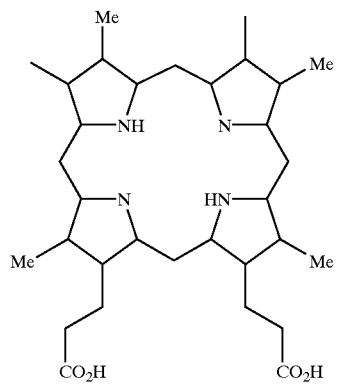

or a salt, ester, amide, or acylhydrazone thereof, which is highly conjugated. It includes the porphyrin system, which is in effect a completely conjugated system; the chlorin system, which is in effect a dihydro form of the porphyrin; and the reduced chlorin system, which is a tetrahydro form of the conjugated porphyrin system. When "porphyrin" is specified, the completely conjugated system is indicated. Green porphyrins are effectively a dihydro form of the porphyrin system.

In one embodiment, the substituent $R^4$ includes at least one additional tetrapyrrole-type nucleus. The resulting compounds of the invention are dimers or oligomers in which at least one of the tetrapyrrole-type ring systems is a green porphyrin. Linkage between the green porphyrin moiety at the $R^4$-position to an additional tetrapyrrole-type ring system may be by an ether, amine or vinyl linkage. Porphyrin ring systems having two available substituent positions (in both A and B rings) corresponding to $R^4$ can be additionally derivatized, as explained below.

When R4 is "—L—P," —L— is selected from the group consisting of:

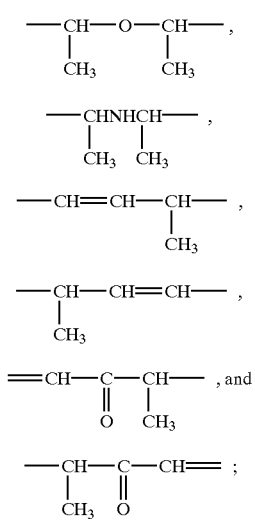

and P is a porphyrin structure or a second green porphyrin of the formulas 1–6 shown in FIG. 6, except that any second $R^4$ group is replaced by L above.

(It is also understood that, when —L— is of the formula (e) or (f) shown above, the ring system to which the double bond is attached will have a resonance system corresponding to

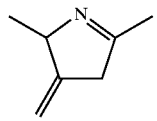

in the ring to which the double bond is attached, as shown.)

The hydro-monobenzoporphyrins that directly result from the Diels-Alder reaction described above can also be isomerized to the BPD compounds of formulas 3 and 4 of FIG. 6. The depictions of compounds 3 and 4 in FIG. 6 do not show the relative position of the exocyclic methyl group (ring A of formula 3 and ring B of formula 4) with respect to the $R^2$ substituent. Either isomer is available. Compounds of formulas 3 and 4 are particularly preferred in the methods and compositions of the invention.

In addition, the Diels-Alder products could be selectively reduced by treating with hydrogen in the presence of a catalyst, such as palladium on charcoal, to give the saturated ring analogs, shown as formulas 5 and 6 in FIG. 6, which correspond to the respective Diels-Alder products of rings A and B. However, as explained above, the more common practice is to perform the Diels-Alder reaction starting with an olefin starting material, in the place of the usual acetylene starting material, to achieve a more reduced form of the resulting porphyrin ring system. The description set forth above with respect to the compounds of formulas 1 and 2 concerning derivatization by conversion of the remaining vinyl substituent ($R^4$) and with respect to the variability of $R^3$ applies as well to the compounds of formulas 3, 4, 5 and 6.

Preferred embodiments of the green porphyrins of the invention are those in which the Diels-Alder product is rearranged and partially hydrolyzed. Even more preferred are the compounds of formulas 3 and 4 (BPD's) in which the carbalkoxy groups in the $R^3$-positions have also been hydrolyzed or partially hydrolyzed. Compounds of the invention that contain —COOH may be prepared as either the free acid or in the form of salts with organic or inorganic bases.

FIG. 7 shows four particularly preferred compounds of the invention covered by formulas 3 and 4, which are collectively designated as benzoporphyrin derivatives, i.e., BPD-DA, BPD-DB, BPD-MA and BPD-MB. These are hydrolyzed or partially hydrolyzed forms of the rearranged products of formula 3 and 4, wherein one or both of the protected carboxyl groups of $R^3$ have been hydrolyzed. The ester groups at $R^1$ and $R^2$ hydrolyze relatively slowly, so that conversion to the forms shown in FIG. 7 is easily effected. The most preferred of these green porphyrin compounds is BPD-MA.

In FIG. 7, $R^3$ is —$CH_2CH_2COOR^{3'}$ where $R^{3'}$ varies by individual compound. Specifically, in BPD-DA, $R^1$ and $R^2$ are carbalkoxy, $R^{3'}$ is hydrogen, and derivatization is at ring A. BPD-DB is the corresponding compound with derivatization at ring B. BPD-MA represents the partially hydrolyzed form of BPD-DA, and BPD-MB represents the partially hydrolyzed form of BPD-DB. Thus, in these latter compounds, $R^1$ and $R^2$ are carbalkoxy, one $R^{3'}$ is hydrogen, and the other $R^{3'}$ is alkyl (1–6C).

The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. In addition, mixtures of any two or more of BPD-MA, -MB, -DA and -DB may be used in the methods of and compositions of the invention.

It should be noted that many of the compounds of FIG. 6 contain at least one chiral center and, thus, may exist as optical isomers. The method of the invention can use compounds having both configurations of the chiral carbons, whether the compounds are supplied as isolates of a single stereoisomer or are mixtures of enantiomers and/or diastereomers. Separation of mixtures of diastereomers may be effected by any conventional means. Mixtures of enantiomers may be separated by any of the usual techniques, such as by reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms, e.g., formula 3 alone or 4 alone, or mixtures in any ratio, may be used in the methods and compositions of the invention.

Further still, dimeric forms of the green porphyrin and dimeric or multimeric forms of green porphyrin/porphyrin combinations can be used to absorb more light on a per mole basis. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Pharmaceutical Composition

Typically, the photosensitizing agent of the invention is formulated into a pharmaceutical composition by mixing the photosensitizing agent, typically at ambient temperatures, appropriate pH's, and the desired degree of purity, with one or more physiologically acceptable carriers, i.e., carriers that are non-toxic to recipients at the dosages and concentrations employed. Suitable compositions include those appropriate for systemic or topical administration, including preparations for injection, transmucosal administration, or transdermal administration.

The composition of the invention preferably comprises about 1 µg/ml to about 2 mg/ml of the photosensitizing agent, depending primarily on the mode of administration. For topical administration, from about 0.1 to about 2.0 mg/mL are preferably used. For systemic administration, e.g., intravenous injection, the concentration of the photosensitizing agent preferably varies from about 0.3 to about 0.5 mg/mL.

Preferably, the photosensitizing agent is administered in a liquid, gel, or gelatinous solid pharmaceutical composition, either alone with water, or together with other pharmaceutically acceptable excipients, such as are disclosed in *Remington's Pharmaceutical Sciences*, Mack Publishing Co., Easton Pa. (Gennaro, ed. 1990), which is hereby incorporated by reference. When a liquid, the pharmaceutical composition containing the photosensitizer can be a suspension or an emulsion. In particular, liposomal or lipophilic formulations are often desirable. The photosensitizing agent of the invention may be included within liposomes, attached to their surface, or both. Suitable methods for preparing liposomes are well-known in the art. The inclusion of green porphyrin compounds in such preparation is described, for example, in Allison et al., U.S. Pat. No. 5,214,036 issued May 25, 1993 and Desai et al., co-pending application Ser. No. 08/489,850 filed Jun. 13, 1995, both of which are incorporated herein by reference. If suspensions or emulsions are used, suitable excipients include water, saline, dextrose, glycerol, and the like. These pharmaceutical compositions may also contain minor amounts of nontoxic auxiliary substances, such as wetting or emulsifying agents, antioxidants, pH buffering agents, and the like.

The pH of the formulation depends mainly on the particular use and the concentration of the photosensitizer, but preferably ranges from about 3 to about 8. Preferably, the photosensitizer is maintained at a neutral pH (e.g., about 6.5 to about 7.5) to prevent its adhering to the contains in which it is placed, as occurs at pH values approaching physiological levels, and to ensure activation of the photosensitizer. Thus, the formulation of a photosensitizer in an electrolyte solution containing a balanced salt buffer at pH 6.5, but containing no fetal bovine serum ("FBS"), is a suitable embodiment. The reason the FBS is omitted is because it contains antigenic components that could exacerbate an inflammatory reaction. If the photosensitizing agent adheres to the containers in which the pharmaceutical composition containing it is being kept, an appropriate non-antigenic ingredient, such as human serum albumin, may optionally be added in an amount that does not interfere with the photosensitizing agent adhering to the injured tissue being treated.

The photosensitizing agent may be combined with one or more immunosuppressive agents to enhance the anti-inflammatory effect on the injured tissue. The term "immunosuppressive agent" as used herein refers to substances that act to suppress or mask T-lymphocyte responses. This would include substances that suppress cytokine production, downregulate or suppress self-antigen expression, or mask the MHC antigens.

Examples of such agents include 2-amino-6-aryl-5-substituted pyrimidines; azathioprine or cyclophosphamide; bromocriptine; glutaraldehyde; anti-idiotypic antibodies for MHC antigens; cyclosporin A; one or more steroids, preferably corticosteroids and glucocorticosteroids such as prednisone, methyl prednisolone, and dexamethasone; anti-interferon-gamma antibodies; anti-tumor necrosis factor-alpha antibodies; anti-tumor necrosis factor-beta antibodies; anti-interleukin-2 antibodies; anticytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodornase; or RNA or DNA from the host.

This immunosuppressive agent may supplement or be used in combination in the same dosage as the photosensitizing agent or a reduced dosage, and may be administered simultaneously or separately, systemically or locally. The effective amount of such other agents is subject to a great deal of therapeutic discretion and depends on the amount of the photosensitizing agent present in the formulation, the type of injury, the type of immunosuppressive agent, the site of delivery, the method of administration, the scheduling of administration, other factors discussed above, and other factors known to practitioners. However, the amount of immunosuppressive agent appropriate for use with the invention is typically lower than that normally advisable for the treatment of like injured tissues.

When an immunosuppressive agent is used, it may be administered by any suitable means, including parenteral and, if desired for local immunosuppressive treatment, intralesionally, i.e. topically to the injured tissues. Parenteral infusions include intramuscular, intravenous, intraarterial, intraperitoneal, subcutaneous, and subconjunctival administration.

If the pharmaceutical composition of the invention is to be applied topically, for example, if it is to be painted onto the injured tissue, it may be preferable to use a viscous solution, such as a gel, rather than a non-viscous solution. The gel may be prepared, for example, by mixing a solution of the desired photosensitizing agent with a gelling agent, such as a polysaccharide, preferably a water-soluble polysaccharide, e.g., hyaluronic acid, starches, and cellulose derivatives (such as methylcellulose, hydroxyethyl cellulose, and carboxy methyl cellulose). When a polysaccharide is present in a gel formulation, the amount usually present is in the range of about 1–90% by weight of the gel, more preferably about 1–20%. Examples of other suitable polysaccharides for this purpose and a determination of the solubility of the polysaccharides are found in EP 267,017 published May 11, 1988, the disclosure of which is incorporated herein by reference.

Examples of suitable surfactants include the poloxamer surfactants, which represent a series of molecules that are block copolymers of ethylene oxide and propylene oxide, either alone or taken in admixture with a phospholipid such as egg lecithin. Another example of an emulsion commercially available from Green Cross is Fluosol-DA 20%, which contains perfluorodecalin and perfluorotripropylamine emulsified with the poloxamer surfactant, Pluronic F-68. The perfluorochemical emulsions and their effects in mammals are described more fully in Bollands et al, *J.*

*Pharm. Pharmacol.*, 39:1021–24 (1987), the disclosure of which is incorporated herein by reference.

The pharmaceutical composition of the invention is preferably sterile. Sterility is readily accomplished by sterile filtration through 0.2 micron membranes. Once formulated and sterilized, the composition may not be stable to oxidative denaturation. However, lyophilized formulations for reconstitution, for example, containing BPD, are suitable for storage.

Modes of Bringing Tissue into Contact with Photosensitizer

The reduction or prevention of inflammation in accordance with the present invention is effected in a relatively straightforward manner by bringing the injured tissue (or the tissue to be injured or being injured) into contact with the photosensitizing agent under conditions that enable the formation of a strong association between the photosensitizing agent and the target tissue, while minimizing the concentration of the photosensitizer and, so far as is practicable, localizing the area of contact to the target injured tissue.

When the cells to be protected from inflammation are contained within a live, intact animal, the photosensitizer may be administered locally or systemically. The photosensitizing agent may be administered by injection so long as the particular mode of injection allows for rapid clearance of the photosensitizer from the body. For example, intravenous injection would be suitable. Alternatively, the photosensitizer may be topically or enterally applied, e.g., by painting or spraying onto the surface of the tissue to be treated, or via patches or implants, which are typically removable at the conclusion of a pre-determined photosensitizer contact time.

When the target tissues to be protected from inflammation are delicate ocular tissues, topical external administration is preferred due to the localized nature of contact with the eye achievable with topical administration, which results in a greater margin of safety. In an especially preferred embodiment, the photosensitizer of the invention is applied with the article of the invention, which comprises the photosensitizer and an absorbent applicator. The absorbent applicator comprises any absorbent material that is sterile or is capable of being sterilized, that easily releases the photosensitizes on contact with injured tissues, and that does not chemically react with the photosensitizing agent. Preferably, the absorbent material is also inexpensive and disposable. Examples of suitable absorbent applicators include drug-soak sponges and non-lint-producing flexible webs. A drug-soak sponge, such as a Weck cell, is the preferred absorbent applicator. When such an applicator is used, it is preferably saturated with the pharmaceutical composition of the invention and topically applied to the target tissues during or shortly after the occurrence of injury, e.g., during a surgical procedure.

The contacting step can take place over a wide variety of temperatures, avoiding only those temperatures great enough to denature or otherwise deleteriously affect the injured tissue and those temperatures low enough to minimize the cellular uptake of the photosensitizer. Preferably, the contacting step takes place at a temperature in the range from about 5° C. to about 40° C., preferably, from about 15° C. to about 37° C. and, most preferably, at ambient temperature.

Dosing

In the method of the invention, the subject is administered an amount of the photosensitizing agent, or a mixture of photosensitizing agents, in one or several dosages. The photosensitizing agents of the invention are dosed in a fashion consistent with good medical practice, taking into account the nature of the inflammation being prevented or reduced, the species and medical condition of the subject, the presence of any other drug in the subject's body, the purity and chemical form of the photosensitizer, the mode of administration, the rate and degree of absorption expected, and other factors known to practitioners. A therapeutically effective amount of photosensitizer is an amount that is effective to reduce significantly, upon exposure to light, the proliferation of fibroblasts, thus ameliorating the inflammatory response and the undesirable effects that may be associated with inflammation, such as increased vascularity and/or scar tissue formation.

The dose of the photosensitizing agent will vary with the target tissue and, if administered intravenously or systemically, will be limited by the weight and optimal blood level of the animal. Suitable systemic amounts per dose are typically less than about 1.0 mg/kg of body weight, preferably in the range of from about 0.25 to 0.75 mg/kg per dose and, most preferably, about 0.15 to about 0.50 mg/kg per dose. A systemic dose of BPD as the photosensitizer would exceed 0.3 mg/kg only under unusual circumstances. These dosage ranges are intended to be suggestive and should not necessarily be considered as limiting, since the individual reactions of particular subjects will also vary.

Depending on the photosensitizing agent and the mode of administration, an equivalent optimal systemic blood level can be established, but it is difficult to do because the photosensitizer preferably clears very rapidly. Thus, there can be a dramatic difference between the concentration of the photosensitizer in the bloodstream at the moment of injection and the concentration at the time of treatment with light. For example, the concentration of BPD at the moment of intravenous injection may range from about 1–10 mg/mL, while, at the time of light exposure, may only be in the range of from 0.5–0.05 ug/mL. If by topical administration, no photosensitizer at all is typically detectable in the blood.

When administered topically or systemically, the dose is best described in terms of the concentration of the composition and the length of the time of contact with the target tissue. A generally effective range of concentrations for the photosensitizing agent is from about 0.1 to about 10 mg/mL, preferably from about 0.1 to about 5 mg/mL and, most preferably, from about 0.25 to about 2.0 mg/ml. The contact suitably involves applying the composition to one or more surfaces of the injured tissue with the pharmaceutical composition of the invention. Topical contact with the photosensitizer generally takes place for at least one minute, preferably under five minutes, and even more preferably from about one to two minutes. The time of contact depends on such factors as the concentration of the photosensitizing agent in the composition, the tissue to be treated, and the particular type of composition.

After a predetermined contact time with the photosensitizer, the excess photosensitizer is preferably removed from the area of treatment. If the photosensitizer is being systemically administered, the photosensitizer is selected to have, not only rapid pharmacokinetic characteristics, but also susceptibility to rapid clearance from the body. If the photosensitizer is being topically administered, the excess is preferably removed by irrigating or flushing away with a physiologically acceptable, chemically inert fluid, such as normal saline or BSS (basic salt solution), or washing off with water or some other solvent. Again, these protocols are not intended to be limiting in view of the wide variation permitted in protocol design.

Following the step of bringing the injured tissue, or pre-injured tissue, into contact with a composition containing the photosensitizer of the invention, the tissue is subjected to exposure with light having a wavelength that is absorbed by the photosensitizing agent and leads to the reduction or prevention of inflammation. The term "low-dose PDT" in this application refers to a dose that does not cause evident cell damage, necrosis or erythema, but exhibits only an anti-inflammatory effect. Because the total PDT dose depends on a combination of the dose of the photosensitizing agent and the dose of the irradiating light, low-dose PDT may be administered in combinations of relatively high photosensitizer doses and low light doses or, on the other hand, combinations of relatively low photosensitizer doses and high light doses. The latter low photosensitizer/high light combination can also be achieved by administering a relatively high dose of photosensitizer, followed by an unusually long "incubation" time before being irradiated with light. Therefore, a wide variety of conditions, all producing a relatively low dose of PDT overall, would be suitable for the invention.

Likewise, a wide variety of different combinations of photosensitizer doses, contact times, and modes of administration are suitable. However, the following rough guidelines may be useful. Short contact (less than one hour) with high doses of the photosensitizer e.g., 2 mg/mL applied topically, would generally be equivalent to a low photosensitizer dose, e.g., 0.15 mg/kg administered intravenously. However, even after a high dose of photosensitizer administered intravenously, delaying irradiation with light to a later time, e.g., more than three hours, after administration of the photosensitizing agent can also result in low-dose PDT because, if the photosensitizer is capable of rapid clearance, very little of it may still be present in the tissues after three hours.

Specific examples of "low-dose PDT" would include:
topical application or localized injection of less than 2 mg/mL of a benzoporphyrin derivative ("BPD") photosensitizer, which is left in contact with the target tissue for less than ten minutes;
intravenous administration of less than 0.15 mg/kg of a BPD with irradiation at any time after administration of the BPD; or
intravenous administration of 0.15–0.50 mg/kg BPD with irradiation more than six hours after BPD administration;
coupled with irradiation under the following conditions:
less than 15 $J/cm^2$ applied between 0–3 hours after administration of the photosensitizer; or
up to 100 $J/cm^2$ applied later than six hours after photosensitizer administration.

During the irradiation step, any light that the photosensitizer absorbs and that is appropriate for use with the injured tissue may be used, e.g., from about 380 to about 850 nm, depending upon the photosensitizer and upon the depth of tissue penetration desired, preferably from about 400 to about 700 nm. For general anti-inflammatory applications, light in the visible portion of the electromagnetic spectrum, e.g., red light, blue light or even UVA light, may be used. Light having a wavelength shorter than 400 nm is acceptable, but not preferred because of the potentially damaging effects of UVA light. Light having a wavelength longer than 700 nm is also acceptable, but not particularly preferred because it is difficult to see, thus making the visual control of irradiation almost impossible. For ocular applications, red light is preferred because this eliminates any potentially harmful effects from the blue and UVA spectral ranges on the sensitive retina of the eye.

An example of a particularly preferred procedure which is used during filtering surgery, is as follows:
1. Saturate a drug-soak sponge with a 2 mg/mL aqueous dispersion of liposomal BPD;
2. Place the BPD-saturated sponge in contact with the tissue to be treated for two minutes;
3. Remove the excess BPD by washing with copious amounts of sterile saline or balanced salt solution; and
4. Expose the BPD-treated tissue to about 7–12 $J/cm^2$ of light.

No single protocol appears to be desirable for all cases at this time. However, typical protocols will include either a single treatment or an initial treatment followed optionally by 1–4 additional treatments. Local treatments with topical photosensitizer administration can be repeated every 3 or 4 days. However, with systemic administration of the photosensitizer, repeated treatments are generally spaced about a week apart, or longer, to avoid any undesirable effects from the accumulation of excess photosensitizer.

The following examples are intended to illustrate, but not to limit, the invention.

EXAMPLES

Example 1

Light Dosing

Filtration surgery was performed on one eye in six normal rabbits. A Weck cell sponge was saturated with a 2 mg/mL aqueous solution of the photosensitizer benzoporphyrin derivative monoacid ring A (BPD-MA, also known as "BPD-verteporfin"). During surgery, the saturated Weck cell was used to apply BPD-MA topically for two minutes to the sclera and conjunctiva in the surgical field. After washing out the excess drug with BSS, both the sclera and conjunctiva were exposed to red light having a wavelength of about 690 nm, which was delivered by a light emitting diode ("LED") placed at a distance of about 1 cm from the tissue to be irradiated. Each of the six rabbits used in this experiment received a different dose of light, specifically, 0, 3, 6, 12, 18 and 24 $J/cm^2$ over a 30-second to 4-minute time period. The treated rabbits were followed for 11–12 days after surgery by determining filtration bleb height, bleb vascularity (indicative of inflammation), and reduction in intraocular pressure ("IOP"). The data obtained on day 5 and day 11 are shown below in Tables 1A and 1B respectively.

TABLE 1A

Results of Pilot BPD-MA for Light Dosing at Postoperative Day 5

| Rabbit No. | Irradiation Time | IOP Decrease (mm Hg) | Bleb Height | Bleb Vascularity |
|---|---|---|---|---|
| 1 | 0 (No BPD) | 2–3 | Moderate | Vascular |
| 2 | 30 seconds | Minimal | Small | Vascular |
| 3 | 1 minute | >20 | Maximum | Avascular |
| 4 | 2 minutes | 20 | Maximum | Avascular' |
| 5 | 3 minutes | 2.5 | Small | Vascular |
| 6 | 4 minutes | 0–4 | Small to Moderate | Vascular |

TABLE 1B

Results of Pilot BPD-MA for Light Dosing at Postoperative Day 11

| Rabbit No. | Irradiation Time | IOP Decrease (mm Hg) | Bleb Height | Bleb Vascularity |
|---|---|---|---|---|
| 1 | 0 (No BPD) | 3–4 | Moderate | Vascular |
| 2 | 30 seconds | 2.3 | Minimal | Vascular |
| 3 | 1 minute | >20 | Maximum | Avascular |
| 4 | 2 minutes | >20 | Maximum | Avascular' |
| 5 | 3 minutes | 3–4 | Low | Vascular |
| 6 | 4 minutes | Sacrificed-bleb failure | | |

The results indicated that the survival of the filtration bleb was the longest in eyes treated with light at a medium range of doses, i.e., relatively low doses of drug and light ("Low-dose PDT"). The data indicated that a certain level of PDT was required, but that higher doses were generally less effective than lower ones. The combination of the short incubation time with BPD and the low light dosage of 12 J/cm$^2$ was not expected to cause much damage to treated cells. Nevertheless, the treatment had a definite pharmacological action. Bleb survival was associated with the lack of inflammation, as indicated by avascularity and a pale-colored bleb.

On the other hand, with too low or too high light doses, the bleb height and the amount of the lowered intraocular pressure were reduced. Bleb failure was associated with inflammation.

Figure 1B:
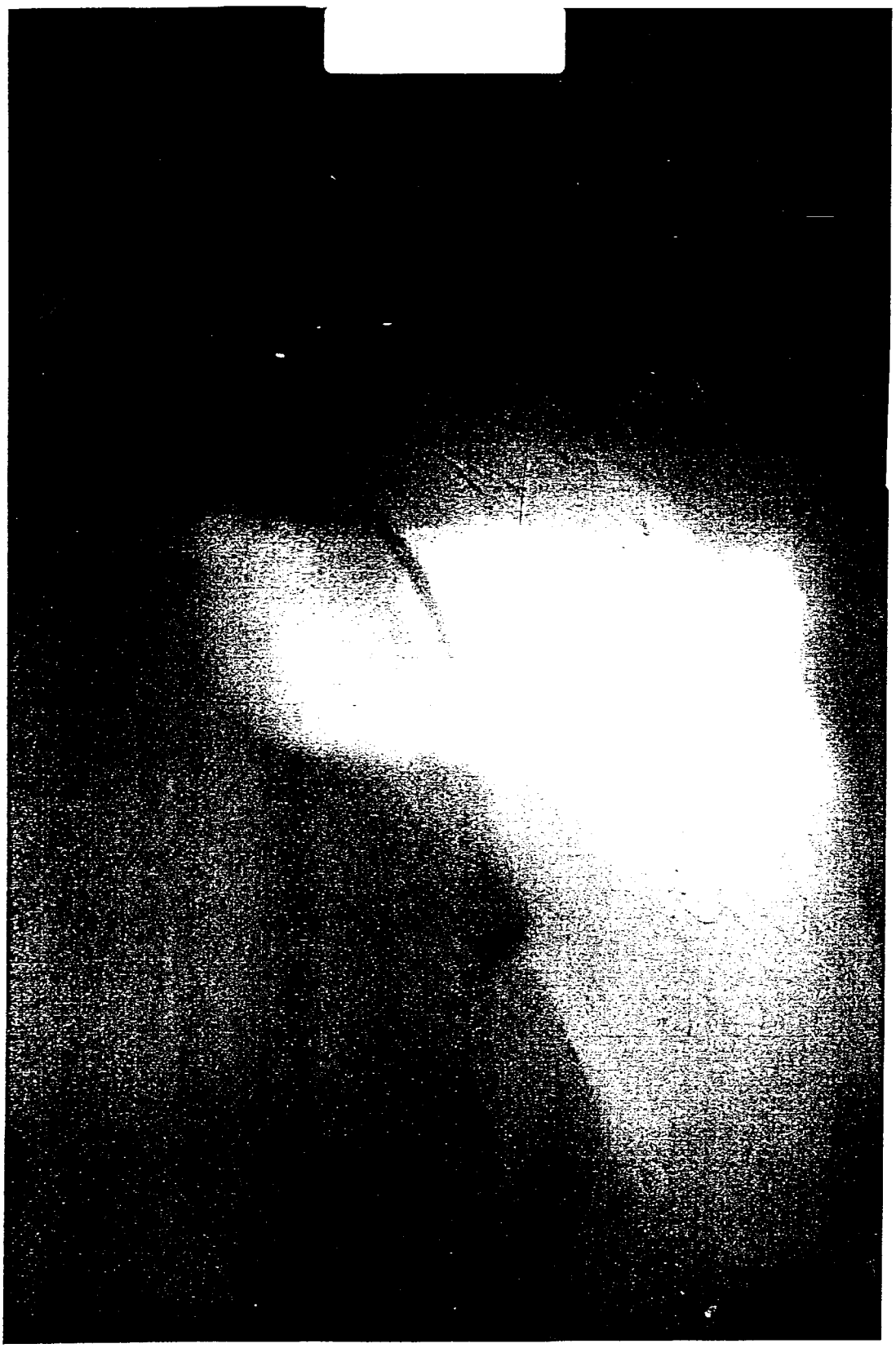
FIG. 1B shows a treated bleb with minimal vascularity and high elevation four days after surgery.

The corresponding filtration blebs are shown in FIG. 1.

Example 2

Times of PDT Administration

The photosensitizer used in the example was prepared as follows: A liposomally formulated benzoporphyrin derivative, monoacid ring A, BPD-MA or BPD-verteporfin was supplied by QLT PhotoTherapeutics, Inc. as a lyophilized powder and was reconstituted with sterile distilled water shortly before use. The BPD was reconstituted to 1.98 mg/mL was used to saturate the 3 mm cut end of a Weck cell. In control groups, the Weck cell was saturated with basic salt solution ("BSS").

On day 0, full thickness filtration surgery was performed on one randomly selected eye in 48 rabbits, 12 in each of four groups. In each rabbit, the untreated other eye served as a control. The filtration procedure was performed in the following manner: Each animal was anesthetized with a mixture of ketamine and xylazine. A wire speculum was used to separate the eyelids. A fornix-based conjunctival flap was created either in the superior nasal or superior temporal quadrant. Following creation of the fornix-based flap, the Weck cell saturated with BPD-MA (or BSS placebo) was placed on the sclera posterior to the limbus where the fistula was to be created. The conjunctiva was draped over the Weck Cell. The Weck cell thus rested between the conjunctiva and sclera, also coming into contact with the episclera and Tenon's capsule, for two minutes. The Weck cell was then removed and the area was irrigated with BSS. Instruments and gloves were also rinsed before entering the eye, and a 1.0 mm trephine was used to enter the anterior chamber.

The conjunctival flap was then secured to the limbus using two 7-0 vicryl sutures. Immediately following surgery, each rabbit had a two-minute exposure of light having a wavelength of 690 nm, with the light source used in Example 1 (Quantum Devices, Inc.) being placed 1 cm from the eye. The light source was used at a maximum output (100 W/cm$^2$), which provided a total dosage of approximately 7.2 J.

A drop of tobramycin was then placed into each eye following surgery. Tobramycin and prednisolone acetate were instilled in both eyes four times a day for one week following surgery.

The control eye received the same photosensitizer and irradiation subconjunctivally as the surgical eye, but without a fistula being created. The control eye was used to test toxicity and as a basis for detecting a decrease in IOP for the surgical eye. The time at which the BPD-MA was applied was varied, as follows:

Group 1: During surgery, placebo treatment;
    48 hours post surgery, placebo treatment;
Group 2: During surgery, BPD treatment;
    48 hours post surgery, placebo treatment;
Group 3: During surgery, placebo treatment;
    48 hours post surgery, BPD treatment;
Group 4: During surgery, BPD treatment; and
    48 hours post surgery, BPD treatment.

BPD treatment at 48 hours post surgery consisted of the application of the 3 mm cut end of a Weck cell saturated with a 2 mg/mL aqueous solution of BPD-MA (or placebo) laid on the conjunctiva over the filtration bleb for two minutes, followed by washing out the excess photosensitizer and exposure to red LED light having a wavelength of 688 nm for one minute.

Postoperatively at day 0 and every two days following surgery, the rabbits were examined with slit lamp biomicroscopy to evaluate filtration bleb extent, filtration bleb height, conjuctival erythema over the bleb, anterior chamber cell flare, and anterior chamber depth. Applanation tonometry to measure IOP following topical anesthesia. A subjective ocular discomfort assessment was also performed by determining animal comfort and eating habits, in accordance with the grading scale shown below:

0: normal behavior
1: head shaking, head tilting, squinting with eyes
2: pawing at eye
3: creating damage/self mutilation (with claws)

Bleb survival was assessed by the extent and height of the bleb and by IOP as compared with the control eye. The degree of the inflammatory response was determined by erythema over the filtration bleb and was scored on a scale of 0–3. Rabbits were terminated when bleb failure was noted, i.e., when the intraocular pressure in the surgical eye equaled that of the control eye and the filtration bleb was flat.

Figure 2:
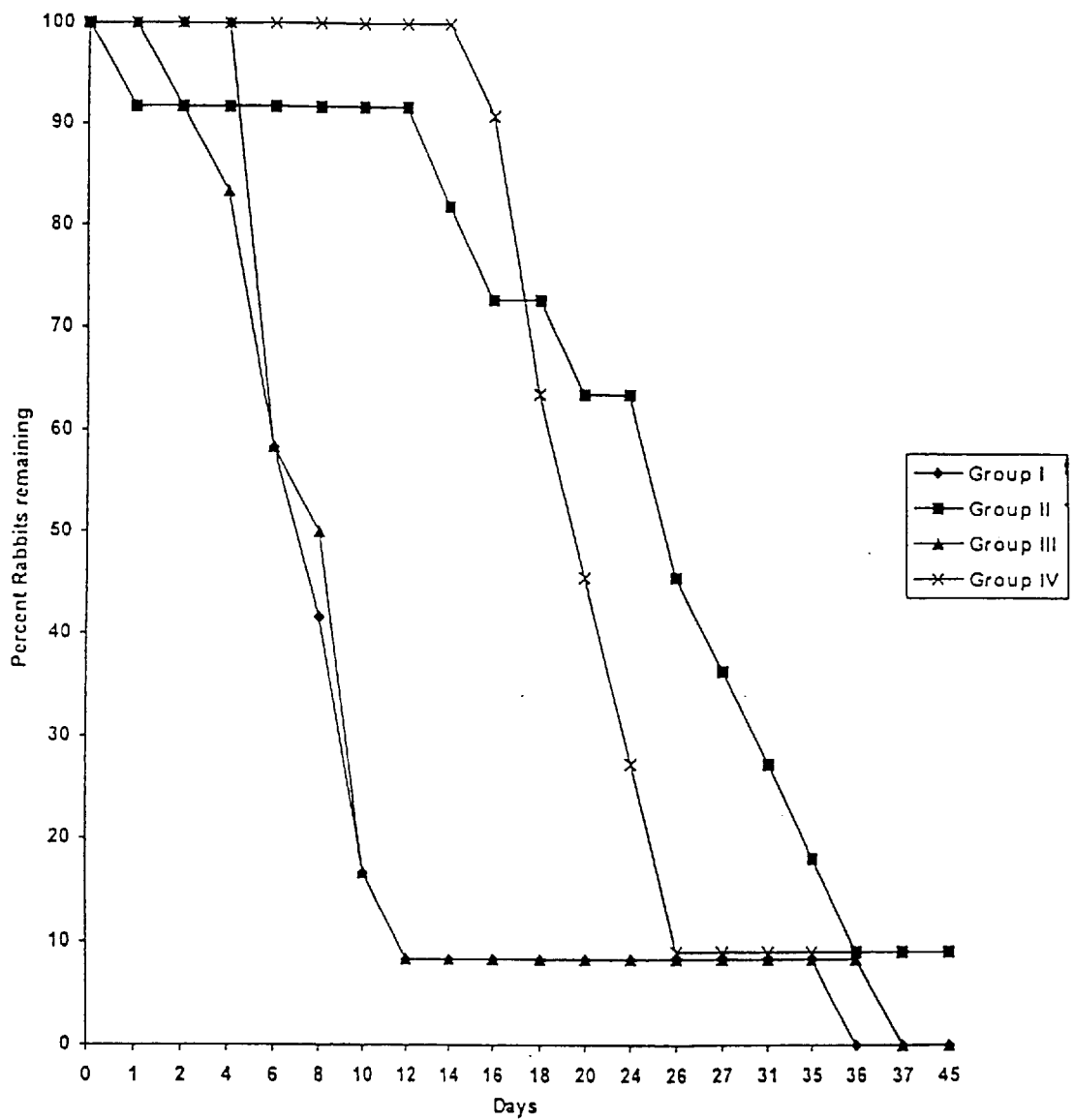
FIG. 2 is a graph showing the percentage of filtration bleb survival of rabbits in each of four groups.

The graph in FIG. 2 shows the percentage of filtration bleb survival of rabbits in each of the four groups evaluated in this study. Mean (±SD) survival times were:

Group 1: 10.3±8 days;
Group 2: 23.8±12 days;
Group 3: 10.1±9 days; and
Group 4: 23.2±8 days.

A statistical difference was observed between most groups (P<0.001), but not between Groups 2 and 4 (P<0.05). Treatment with BPD and light during surgery (Groups 2 and 4) resulted in prolonged bleb survival in comparison with the placebo control (Group 1) or treatment only at 48 hours post surgery (Group 3). The second treatment with BPD and light at 48 hours (Group 4) did not appear to have any additional effect. A Kruskal-Wallis test for non-parametric analysis was used to evaluate differences in the survival time of filtration blebs between groups.

Figure 3:
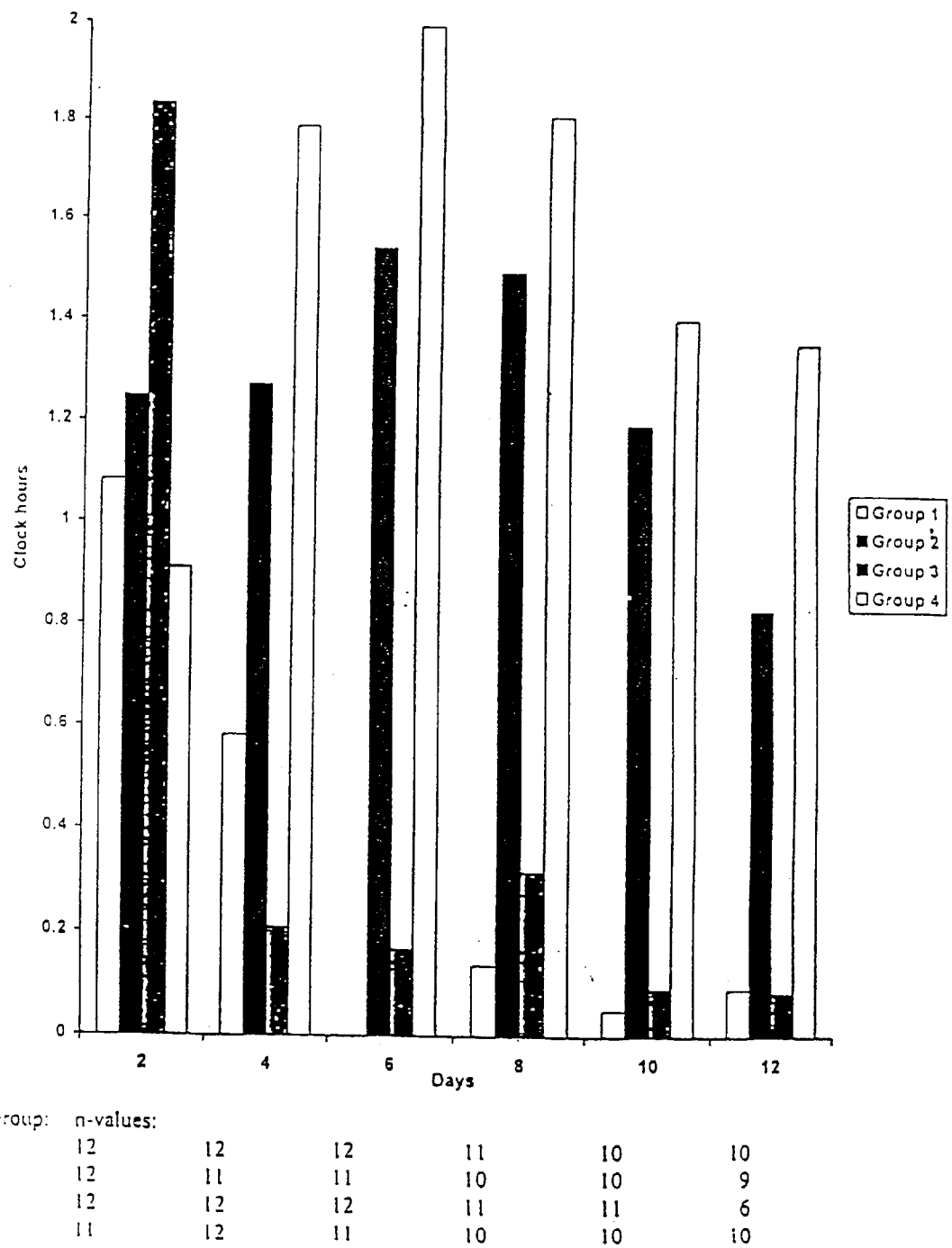
FIG. 3 is a graph showing the differences between groups with respect to bleb extent at each examination day up to 12 days postoperatively.
Figure 4:
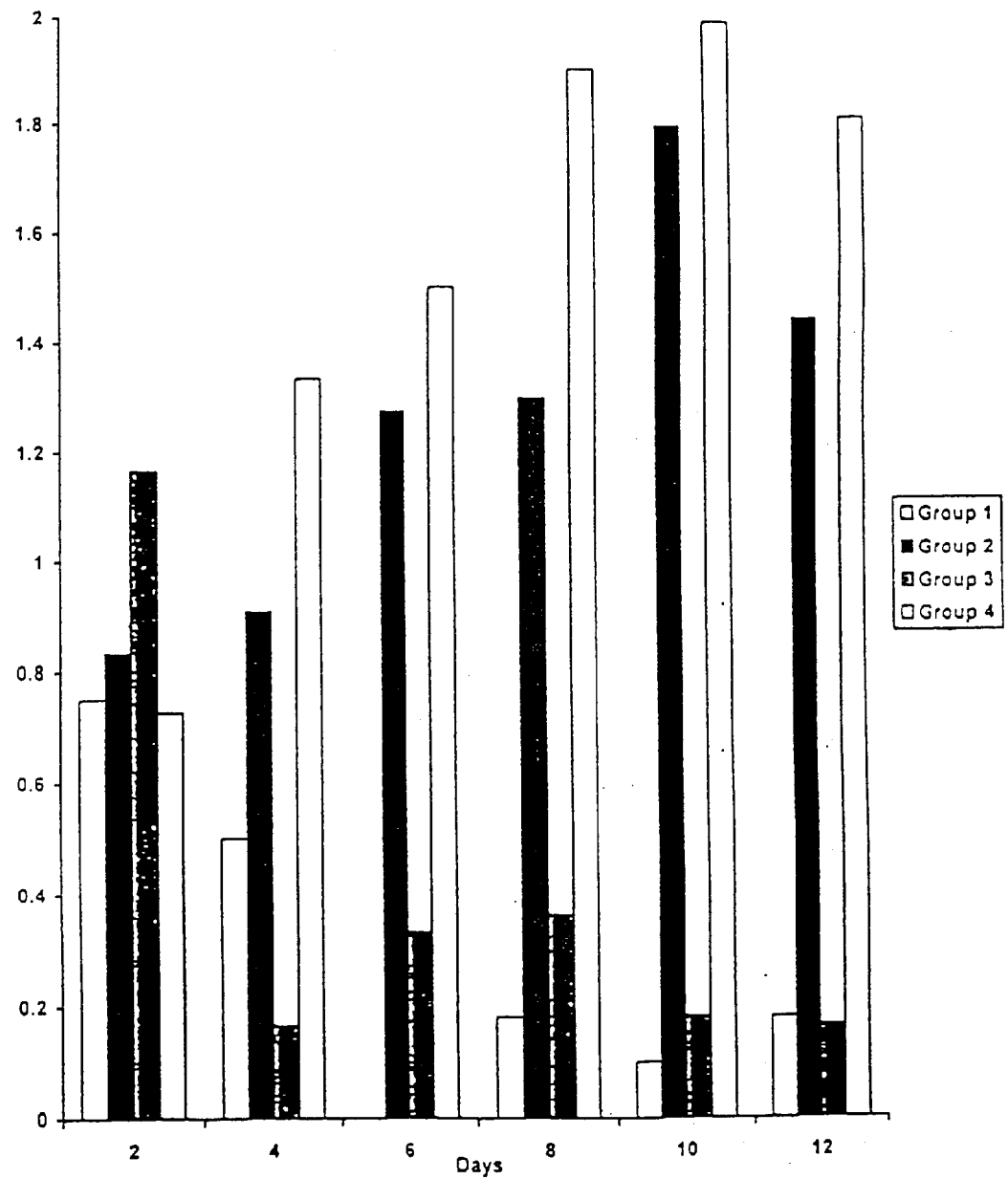
FIG. 4 is a graph showing the differences among groups with respect to bleb height on each examination day up to 12 days postoperatively.
Figure 5:
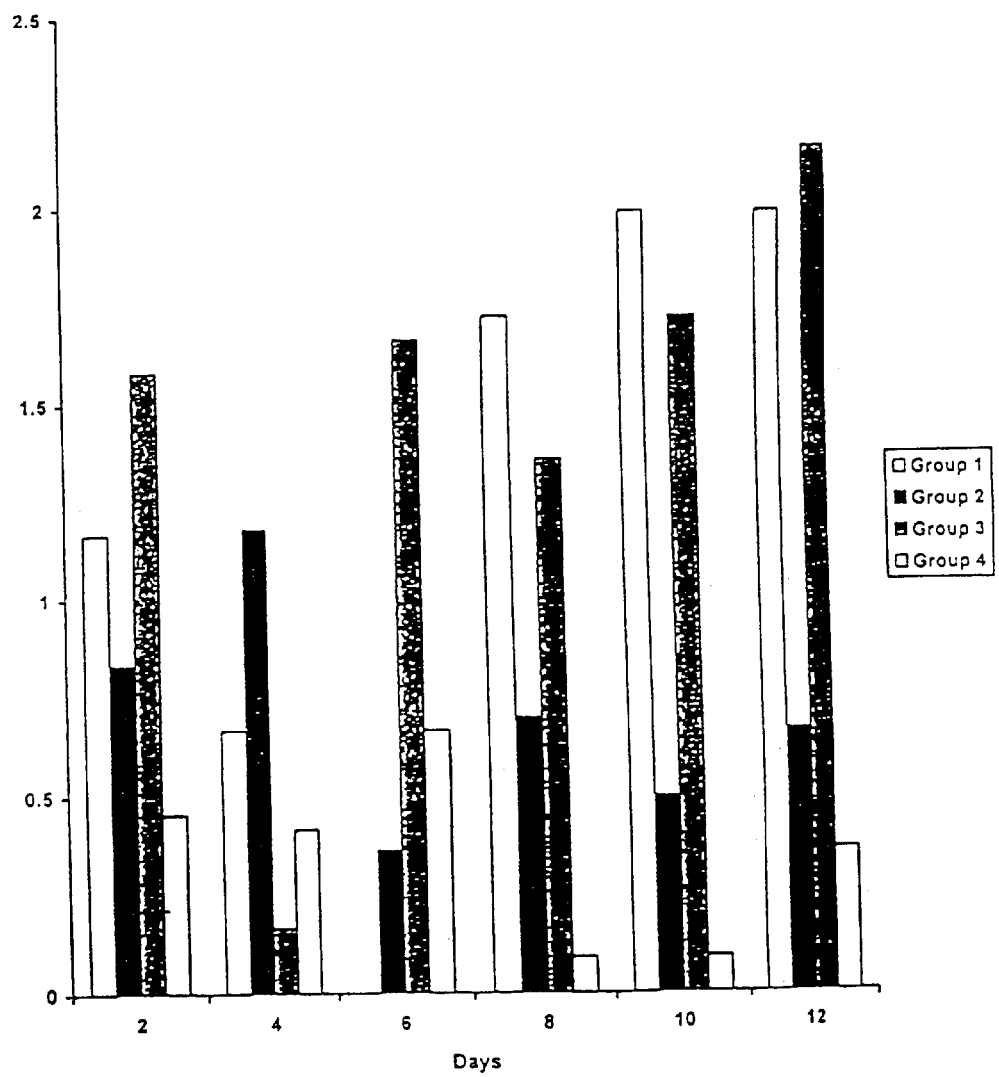
FIG. 5 is a graph showing the differences in conjunctival erythema over the filtration bleb at each examination day up to 12 days postoperatively.

IOP was evaluated by an ANOVA test, and a trend toward lower IOP was observed when BPD was given intraoperatively (P=0.057). However, due to problems with the tonometer used to measure IOP in the rabbits, the most reliable parameters were the extent (FIG. 3) and height (FIG. 4) of the bleb, both which indicated the effectiveness of low-dose PDT treatment during surgery. The measurement of erythema over the bleb (shown in FIG. 5) indicated a higher inflammatory response in Groups 1 and 3, in which blebs failed early post surgery. In FIGS. 3, 4 and 5, a statistical difference was observed between groups (P,0.001). The bleb height and extent, as well as other slit lamp characteristics, were analyzed by a chi-square test. Adverse events also were analyzed by a chi-square test. A Cox Proportional Hazard Model was used to evaluate for parameters that most accurately predicted filtration bleb survival on each examination day.

When compared to previous rabbit studies that have investigated adjunctive medicines for trabeculectomy, as shown below in Table 2, the results showed that BPD prolonged the filtration bleb survival compared to normal controls, Ara-A and 5-fluorouracil.

TABLE 2

| Antifibrotic Therapy | Filtration Bleb Survival (mean days ± SD [range]) | Documents |
|---|---|---|
| No drug | 12.06 ± 6.2 (6–23.2) | Kay et al., "Delivery of Antifibroblast Agents as Adjuncts to Filtration Surgery-Part II: Delivery of 5-Fluorouracil and Bleomycin in a Collagen Implant: Pilot Study in the Rabbit", Ophthalmic Surg., 17:796–801 (1986); Khaw et al., "Effects of Inoperative 5-Fluorouracil or mitomycin C on Glaucoma Filtration Surgery in the Rabbit", Ophthalmology, 100:367–72 (1993); Bergstrom et al., "The Effects of Subconjunctival Mitomycin-C on Glaucoma Filtration Surgery in Rabbits", Arch. Ophthalmol., 109:1725–30 (1991); and Liang et al., "Comparison of Mitomycin C and 5-Fluorouracil on Filtration Surgery Success in Rabbit Eyes", J. Glaucoma, 1:87–93 (1992). |
| 5-Fluorouracil | 19.5 ± 5.5 (14–25) | Kay et al., "Delivery of Antifibroblast Agents as Adjuncts to Filtration Surgery-Part II: Delivery of 5-Fluorouracil and Bleomycin in a Collagen Implant: Pilot Study in the Rabbit", Ophthalmic Surg., 17:796–801 (1986); Khaw et al., "Effects of Inoperative 5-Fluorouracil or mitomycin C on Glaucoma Filtration Surgery in the Rabbit", Ophthalmology, 100:367–72 (1993). |
| Bleomycin | 25.5 ± 14.5 (21–50) | Khaw et al., "Effects of Inoperative 5-Fluorouracil or Mitomycin C on Glaucoma Filtration Surgery in the Rabbit", Ophthalmology, 100:367–72 (1993). |
| Mitomycin-C | 34.8 ± 28.8 (6–23.2) | Khaw et al., "Effects of Inoperative 5-Fluorouracil or mitomycin C on Glaucoma Filtration Surgery in the Rabbit", Ophthalmology, 100:367–72(1993); Liang et al., "Comparison of Mitomycin C and 5-Fluorouracil on Filtration Surgery Success in Rabbit Eyes", J. Glaucoma, 1:87–93 (1992). |
| Ara-A | 15.2 ± 1.8 | Lee et al., "Effects of Cytosine Arabinoside-impregnated Bioerodible Polymers on Glaucoma Filtration Surgery in Rabbits", J. Glaucoma, 2:96–100 (1993). |

The results also showed that BPD prolonged the life of the filtration bleb in rabbits longer that in some rabbits who received mitomycin C. The mean survival time of studies with mitomycin C were longer, and this is consistent with the hypothesis that PDT clinically would cause less overfiltration than mitomycin C but have a similar ease of application with greater safety.

The data indicated clearly that longer bleb survival was associated with no erythema or only minimal erythema and, thus, with the reduction of the inflammatory response. The data also suggested that the treatment with BPD and light, at relatively low ranges of doses, prevented the development of inflammation, especially when administered during surgery.

Adverse events were few and not related specifically to the use of the photosensitizer. A fibrin clot within the first four days was observed in six rabbits, three of which were in Group 2 and three in Group 3. In each case, the fibrin was resolved without sequelae by the end of the first week. One rabbit died at day 0, which was felt to be a complication of anesthesia. No other adverse events were reported.

At day 7, one rabbit from each group and, following bleb failure, two rabbits from each group, were sacrificed to undergo histologic and transmission electron microscopic ("TEM") analysis. Histologic evaluation was performed after first fixing the cadaver eyes with 10% buffered neutral formalin. The eyes were processed, sectioned, and then stained with hematoxylin and eosin, as well as Masson's Trichrome. The specimens were examined in a masked fashion by an independent observer.

Transmission electron microscopy was performed by fixing tissue samples in 2.5% glutaraldehyde buffered with 0.1 M cacodylate containing 7% sucrose. Tissues were post fixed for one hour with 2% osmium tetroxide and dehydrated through graded alcohol concentrations to 100% ethanol. The 2×5 mm tissue blocks were then infiltrated with catalyzed epoxy resin. Thick sections (0.5 $\mu$m) were cut and stained with toluidine blue and examined by light microscopy to determine appropriate areas. Thin section (80 nm)

were then cut, picked up on copper grids, and stained with uranyl acetate and lead citrate for TEM evaluation. A Hitachi H7000 transmission electron microscope was used to examine these sections.

A light microscopy at day 7 postoperatively in filtering blebs that received BPD rather than the placebo at surgery showed that fibroblasts and a mild lymphocytic response were present in the rabbit that received a placebo at both day 0 and day 2. In addition, at day 7, these eyes demonstrated some vascular proliferation and new collagen deposition.

In contrast, the rabbit that received BPD only at day 2 (Group 3), showed increased lymph channels in addition to the fibroblasts, but no vascular proliferation. In both eyes that received BPD at surgery, the filtration bleb was noted to have a mild lymphocytic response. However, no fibroblasts, vascular increase or lymphocytic channel increase were noted. At the end of the study (three weeks postoperatively), in eye fistulas that had received BPD, only a few lymphocytes and no proliferation of blood vessels at the fistula were noted.

In Groups 2 and 4, both at day 7 and at sacrifice, a thinned epithelium was observed. However, this was felt to be due to the elevated bleb and the associated breakdown of the tear fill, as opposed to a toxic effect from the PDT treatment.

In the control eye, no differences between the placebo and BPD-treated eyes were observed in the anterior segment ocular exam, indicating a lack of toxicity of the method or composition of the invention clinically (P>0.05). Additionally, histologic and transmission electron microscopic analysis showed no evidence of toxicity or inflammation apart from the filtration site, either in the surgical or control eye. Therefore, no toxicity from BPD was observed clinically, histologically, or by transmission electron microscopy.

We claim:

1. A method for reducing or preventing the effects of inflammation arising from injured tissue, which method comprises the steps of:
   a. contacting the injured tissue with a green porphyrin photosensitizing agent capable of penetrating into the injured tissue and causing the desired pharmacological effect in less than one hour; and
   b. exposing the contacted injured tissue to light having a wavelength absorbed by the photosensitizing agent for a time sufficient to reduce or prevent inflammation in the exposed tissue, but not so long as to cause necrosis or erythema of the exposed injured tissue.

2. The method of claim 1 wherein the injured tissue is ocular tissue.

3. The method of claim 1 wherein the photosensitizing agent comprises one or more monohydrobenzoporphyrin compounds.

4. The method of claim 1 wherein the photosensitizing agent comprises BPD-MA.

5. The method of claim 1, wherein said contacting step a. is accomplished by topical application of the photosensitizing agent.

6. The method of claim 5, wherein the photosensitizing agent is in the form of a solution having a concentration of 2 mg/mL or less.

7. The method of claim 5, wherein the injured tissue is contacted with the photosensitizing agent by a drug-soak sponge.

8. The method of claim 5 wherein, in said contacting step a., the photosensitizing agent is left in contact with the injured tissue for less than five minutes.

9. The method of claim 1, wherein said step a. is accomplished by systemic administration.

10. The method of claim 9 wherein the dose of the photosensitizing agent is less than 0.30 mg/kg.

11. The method of claim 1 wherein, between said contacting step a. and said exposing step b., the excess photosensitizing agent in contact with the injured tissue is removed.

12. The method of claim 11 wherein said removal is accomplished by flushing away the photosensitizing agent with sterile saline or a balanced salt solution.

13. The method of claim 1 wherein at least some of the wavelengths of the light are in the visible portion of the electromagnetic spectrum.

14. The method of claim 1 wherein the dose of the light during said exposing step b. is less than about 100 $J/cm^2$.

15. The method of claim 1 wherein the time between said contacting step a. and said exposing step b. is between about 0 and three hours, and the dose of the light during said exposing step b. is less than about 15 $J/cm^2$.

16. The method of claim 15 wherein the dose of the light said exposing step b. is about 7–12 $J/cm^2$.

17. The method of claim 1 wherein the time between said contacting step a. and said exposing step b. is greater than about six hours, and the dose of the light during said exposing step b. is from about 15 to 100 $j/cm^2$.

* * * * *